(12) United States Patent
Nishide et al.

(10) Patent No.: US 9,227,892 B2
(45) Date of Patent: Jan. 5, 2016

(54) ORGANIC COMPOUND AND ORGANIC LIGHT-EMITTING DEVICE INCLUDING THE SAME

(75) Inventors: Yosuke Nishide, Kawasaki (JP); Hirokazu Miyashita, Tokyo (JP); Jun Kamatani, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 748 days.

(21) Appl. No.: 13/576,126

(22) PCT Filed: Jan. 12, 2011

(86) PCT No.: PCT/JP2011/050801
§ 371 (c)(1),
(2), (4) Date: Jul. 30, 2012

(87) PCT Pub. No.: WO2011/096272
PCT Pub. Date: Aug. 11, 2011

(65) Prior Publication Data
US 2012/0299806 A1 Nov. 29, 2012

(30) Foreign Application Priority Data
Feb. 2, 2010 (JP) .................................. 2010-021269

(51) Int. Cl.
| | |
|---|---|
| C07C 13/72 | (2006.01) |
| C09K 11/06 | (2006.01) |
| H01L 51/54 | (2006.01) |
| H01L 51/00 | (2006.01) |
| H05B 33/14 | (2006.01) |
| H01L 51/50 | (2006.01) |

(52) U.S. Cl.
CPC ................. *C07C 13/72* (2013.01); *C09K 11/06* (2013.01); *H01L 51/0056* (2013.01); *H05B 33/14* (2013.01); *C09K 2211/1011* (2013.01); *H01L 51/5012* (2013.01)

(58) Field of Classification Search
CPC .................................. C07C 13/62; C07C 13/72
USPC ............................................................ 585/27
See application file for complete search history.

(56) References Cited

U.S. PATENT DOCUMENTS
2011/0198989 A1* 8/2011 Nishide et al. ................ 313/504

FOREIGN PATENT DOCUMENTS
| | | |
|---|---|---|
| JP | 9-241629 A | 9/1997 |
| JP | 2005-68087 A | 3/2005 |
| JP | 2009-280522 A | 12/2009 |
| WO | 2008/059713 A1 | 5/2008 |

* cited by examiner

*Primary Examiner* — Marie R. Yamnitzky
(74) *Attorney, Agent, or Firm* — Canon U.S.A. Inc., IP Division

(57) ABSTRACT

Provided are a novel organic compound appropriate for emission of blue light and an organic light-emitting device including the organic compound. The organic compound is represented by general formula 1:

[Chem. 1]

General formula 1

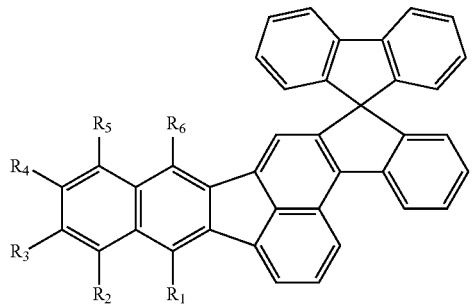

wherein $R_1$ to $R_6$ are each independently selected from a hydrogen atom, an alkyl group, and an aryl group. The alkyl group and the aryl group are optionally substituted.

9 Claims, 1 Drawing Sheet

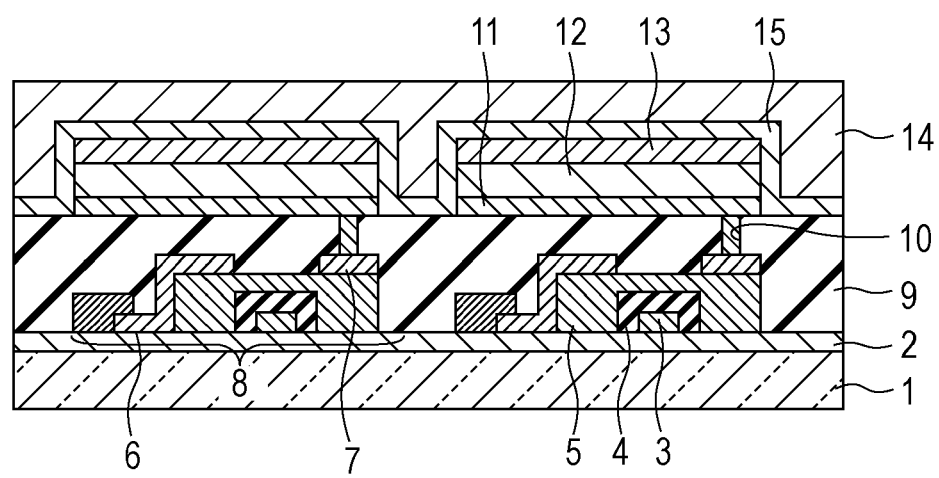

ORGANIC COMPOUND AND ORGANIC LIGHT-EMITTING DEVICE INCLUDING THE SAME

TECHNICAL FIELD

The present invention relates to novel organic compounds and organic light-emitting devices including such organic compounds.

BACKGROUND ART

Organic light-emitting devices include a pair of electrodes and an organic compound layer disposed therebetween. When the pair of electrodes inject electrons and holes into the organic compound layer, a luminous organic compound contained therein generates excitons and emits light as they return to the ground state.

Organic light-emitting devices are also referred to as organic electroluminescent (EL) devices.

PTL 1 discloses IK-12, shown below, as an example of an organic compound constituting a light-emitting layer. This compound has benzo[k]fluoranthene, shown below, as the basic backbone thereof. Benzo[k]fluoranthene itself, that is, unsubstituted benzo[k]fluoranthene, emits light in the ultraviolet region and does not emit visible light. According to Patent Literature 1, IK-12 emits blue light as a result of substitution of the basic backbone with tert-butyl groups. IK-12 has phenyl groups at the 7- and 12-positions thereof and tert-butyl groups at the 2-, 5-, and 9-positions thereof. This inhibits concentration quenching due to molecular aggregation.

[Chem. 1]

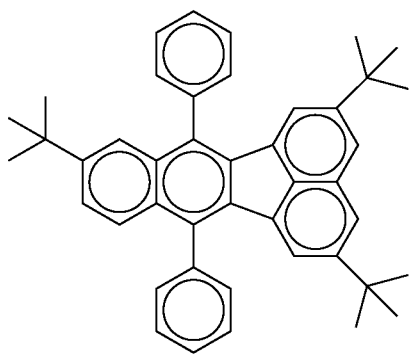

(IK-12)

[Chem. 2]

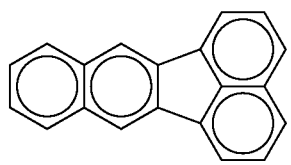

(Basic backbone)

IK-12 disclosed in PTL 1 has the basic backbone thereof, namely, benzo[k]fluoranthene, substituted so that it can emit blue light. However, substituents such as tert-butyl groups may impair chemical stability.

CITATION LIST

Patent Literature

PTL 1 Japanese Patent Laid-Open No. 9-241629 (no foreign counterpart)

SUMMARY OF INVENTION

Accordingly, the present invention provides a novel organic compound having a newly created basic backbone that allows the compound to emit blue light by itself while having high chemical stability.

A novel organic compound according to an aspect of the present invention is represented by general formula 1:

[Chem. 3]

General formula 1

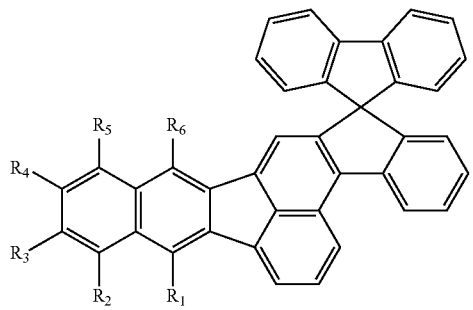

In general formula 1, $R_1$ to $R_6$ are each independently selected from a hydrogen atom, an alkyl group, and an aryl group; the alkyl group is methyl, ethyl, n-propyl, isopropyl, n-butyl, isobutyl, sec-butyl, or tert-butyl; the aryl group is phenyl, biphenyl, terphenyl, naphthyl, phenanthrenyl, anthracenyl, fluoranthenyl, benzofluoranthenyl, or fluorenyl; the alkyl group and the aryl group are optionally substituted with an alkyl group, an aryl group, an aralkyl group, a heterocyclic group, an amino group, a cyano group, an alkoxyl group, or a halogen atom.

According to the present invention, a novel organic compound capable of emitting blue light only with the basic backbone thereof can be provided. In addition, an organic light-emitting device including such a novel organic compound can be provided.

BRIEF DESCRIPTION OF DRAWING

FIGURE is a schematic sectional view of organic light-emitting devices and switching devices connected to the organic light-emitting devices.

DESCRIPTION OF EMBODIMENTS

A novel organic compound according to the present invention is represented by general formula 1:

[Chem. 4]

General formula 1

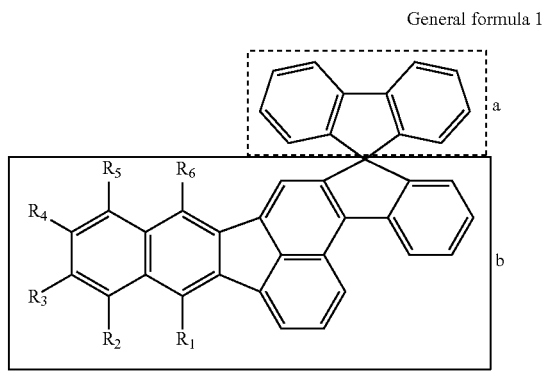

In general formula 1, $R_1$ to $R_6$ are each independently selected from a hydrogen atom, an alkyl group, and an aryl group. The alkyl group and the aryl group are optionally substituted.

The alkyl group is, for example, methyl, ethyl, n-propyl, isopropyl, n-butyl, isobutyl, sec-butyl, or tert-butyl. In particular, the alkyl group may be tert-butyl because it provides a significant effect of inhibiting stacking by steric hindrance.

The aryl group is, for example, phenyl, naphthyl, indenyl, biphenyl, terphenyl, phenanthrenyl, fluorenyl, anthracenyl, pyrenyl, fluoranthenyl, benzofluoranthenyl, or perylenyl. In particular, the aryl group may be phenyl, biphenyl, or terphenyl because they provide a significant effect of inhibiting stacking and hardly affect the emission wavelength.

The alkyl group and the aryl group are optionally substituted with, for example, an alkyl group such as methyl, ethyl, or propyl; an aralkyl group such as benzyl or phenethyl; an aryl group such as phenyl, biphenyl, naphthyl, phenanthrenyl, fluorenyl, pyrenyl, or fluoranthenyl; a heterocyclic group such as thienyl, pyrrolyl, or pyridyl; an amino group such as dimethylamino, diethylamino, dibenzylamino, diphenylamino, ditolylamino, or dianisolylamino; an alkoxyl group such as methoxyl, ethoxyl, propoxyl, or phenoxyl; a cyano group; a nitro group; or a halogen atom such as a fluorine or chlorine atom. In particular, the aryl group may be substituted with methyl, ethyl, propyl, or butyl, more particularly methyl or tert-butyl.

The organic compound according to the present invention can emit blue light only with the basic backbone thereof. The term "basic backbone" as used herein refers to a backbone composed only of fused rings. That is, the term "basic backbone" as used herein refers to a portion represented by rings excluding $R_1$ to $R_6$ in general formula 1.

A compound capable of achieving the intended emission wavelength only with the basic backbone thereof is advantageous in view of stability. Although it is known that the basic backbone of a certain compound can be substituted to achieve the intended emission wavelength, the substitution for changing the emission wavelength may impair the stability of the compound.

The term "blue region" as used herein refers to the wavelength range of 430 to 480 nm.

The organic compound according to the present invention has high chemical stability.

The organic compound according to the present invention has a spiro structure, that is, a structure in which the plane a and the plane b in general formula 1 cross each other, specifically, extend perpendicularly.

The organic compound according to the present invention can be used as a light-emitting material for an organic light-emitting device.

The organic compound according to the present invention has high quantum yield because it has no rotatable bond in the basic backbone thereof and also inhibits molecular aggregation because it has a nonplanar structure.

Thus, the organic compound according to the present invention can be used in high concentrations as a light-emitting material for an organic light-emitting device.

The angle between the plane a and the plane b calculated by a molecular orbital calculation was 89.9 degrees. This demonstrates that the two planes are perpendicular.

In the molecular orbital calculation, the most stable conformation was determined by the following technique.

The above molecular orbital calculation was performed using Gaussian 03 (Gaussian 03, Revision D.01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004), which is currently widely used, by selecting the DFT basis function 6-31+G(d).

Comparison Between Spiro-Containing Compound A1 of Invention and Other Organic Compounds Benzo[k]fluoranthene and an organic compound having a Spiro structure according to the present invention will now be compared.

Benzo[k]fluoranthene, a comparative compound, is represented by the following structural formula:

[Chem. 5]

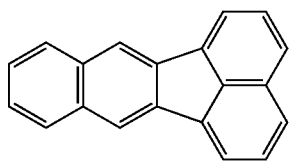

On the other hand, an organic compound A1 according to the present invention is represented by the following structural formula:

[Chem. 6]

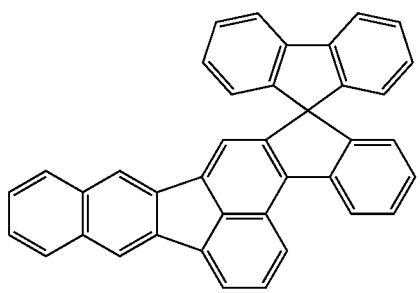

(A1)

The organic compound A1 according to the present invention has a maximum emission wavelength of 442 nm. On the other hand, benzo[k]fluoranthene has a maximum emission wavelength of 410 nm. That is, the maximum emission wavelength of the organic compound according to the present invention falls within the blue region, namely, 430 to 480 nm. On the other hand, the maximum emission wavelength of the comparative organic compound deviates from the blue region to the shorter wavelength.

This means that the compound A1 according to the present invention emits light having a maximum emission wavelength of 430 to 480 nm by itself. Thus, the organic compound according to the present invention can emit blue light in a wavelength range falling within and narrower than the blue region, namely, 430 to 480 nm, only with the basic backbone thereof.

The measured maximum emission wavelengths and half-widths of the organic compound A1 according to the present invention and benzo[k]fluoranthene are shown in Table 1 below.

TABLE 1

| | Maximum emission wavelength (half-width) (nm) | | |
| --- | --- | --- | --- |
| | Dilute (toluene) solution | Spin coating film | Difference in half-width (nm) |
| A1 | 442 (55) | 483 (71) | 16 |
| Benzo[k]fluoranthene | 410 (21) | 487 (94) | 73 |

According to Table 1, the difference between the maximum emission wavelengths of A1 in solution and in thin film was 41 nm. On the other hand, the difference between the maximum emission wavelengths of benzo[k]fluoranthene in solution and in thin film was 77 nm. That is, the wavelength variation of A1 was smaller than that of benzo[k]fluoranthene.

In addition, according to a comparison of the half-widths of A1 and benzo[k]fluoranthene, the shape of the emission spectra of benzo[k]fluoranthene was considerably broadened in thin film, and the increase in half-width was 73 nm. On the other hand, the shape of the emission spectra of A1 was less broadened in thin film, and the increase in half-width was only 16 nm.

The above results indicate that molecular aggregation is weaker in an aggregated state such as thin film for the organic compound A1 according to the present invention than for benzo[k]fluoranthene.

This is because the molecules aggregate and form a new energy level more easily with a shorter intermolecular distance, thus broadening the shape of the emission spectra.

Thus, the present invention can be used for blue light-emitting devices.

The organic compound according to the present invention has a nonplanar structure only with the basic backbone thereof, thus inhibiting molecular aggregation.

Next, IK-12 disclosed in Patent Literature 1 and the organic compound having a spiro structure according to the present invention will be compared. IK-12, a comparative compound, is represented by the following structural formula:

[Chem. 7]

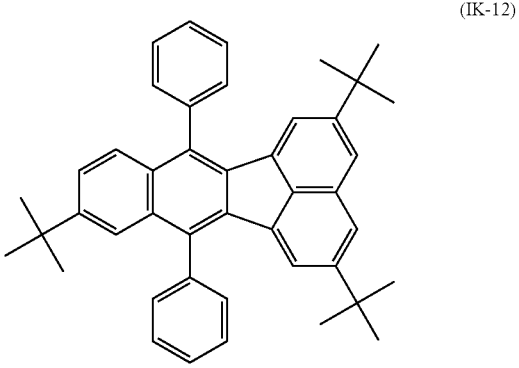

(IK-12)

As shown later in Example 2, an organic light-emitting device formed using A1 as a light-emitting dopant has a half-lifetime of 400 hours at an initial luminance of 7,000 cd/m$^2$. On the other hand, an organic light-emitting device formed using the above comparative compound has a half-lifetime of 660 hours at an initial luminance of 300 cd/m$^2$. It is obvious that the device formed using the compound A1 according to the present invention has a higher durability and longer half-lifetime.

This means that the compound according to the present invention is more stable than the above comparative compound. Thus, because the organic compound according to the present invention has no rotatable bond in the basic backbone thereof, it can be used as, for example, a light-emitting material to form an organic light-emitting device having a longer lifetime.

IK-12 has three tert-butyl groups, serving as electron donors, attached to the basic backbone thereof to emit blue light. It is known that a C(aryl group)-C(alkyl group) bond has a lower bond dissociation energy than a C=C (aromatic ring) bond. In particular, a compound having a stable bond can be used as a blue light-emitting material because high energy is communicated.

The organic compound according to the present invention is used as a guest or host material for a light-emitting layer.

The organic compound according to the present invention can be used as a guest material for a light-emitting layer of an organic light-emitting device. In particular, the organic compound can be used as a guest material for a blue light-emitting device. The organic compound can also be used as an assist material. In addition, the organic compound can be used as any of the layers other than the light-emitting layer, including a hole injection layer, a hole transport layer, a hole/exciton blocking layer, an electron transport layer, and an electron injection layer.

The organic compound according to the present invention can also be used as a host material for a green or red light-emitting layer because the basic backbone itself has a wide band gap.

The term "host material" as used herein refers to a material contained in the highest weight percentage in a light-emitting layer. The term "guest material" as used herein refers to a material contained in a lower weight percentage than a host material in a light-emitting layer and serving as a main component for emitting light.

Examples of Organic Compounds According to Invention

Examples of compounds of general formula 1 above are shown below, although the invention is not limited thereto.

[Chem. 8]

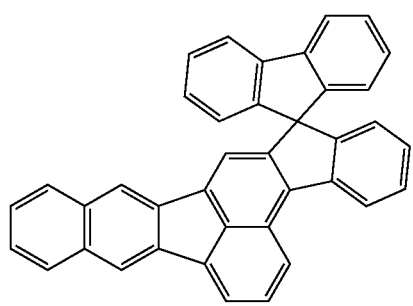

A1

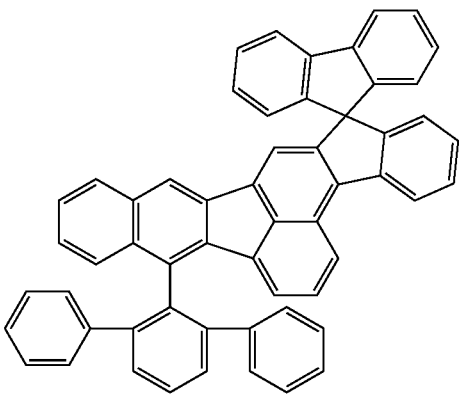

A4

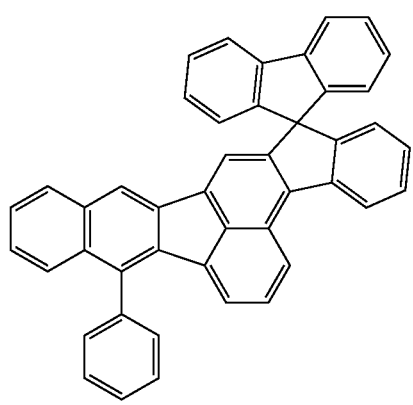

A2

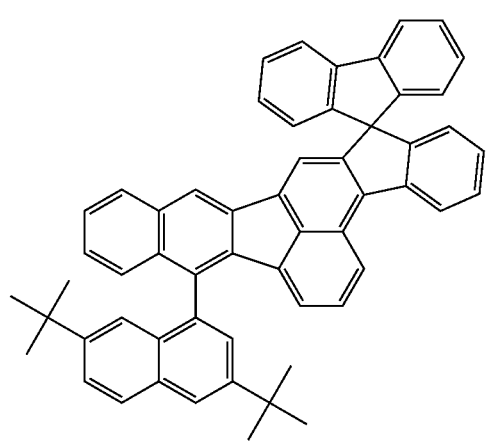

A5

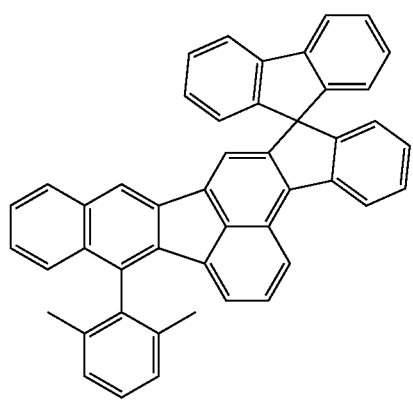

A3

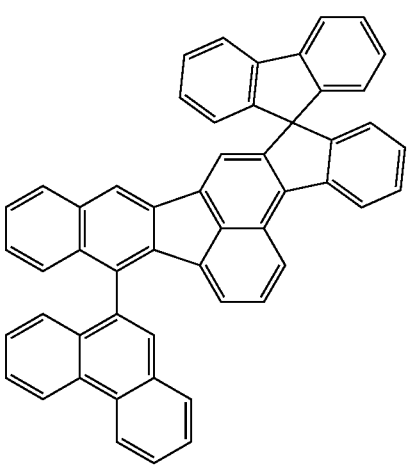

A6

A7
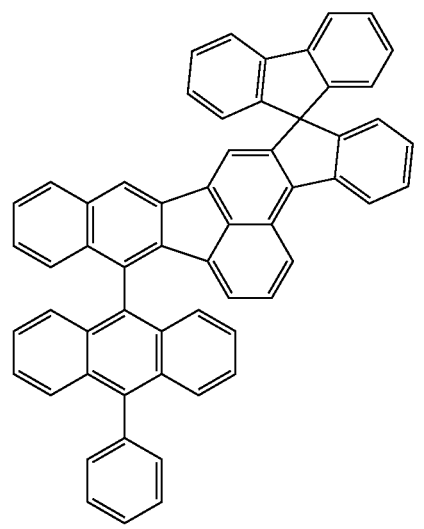
A8
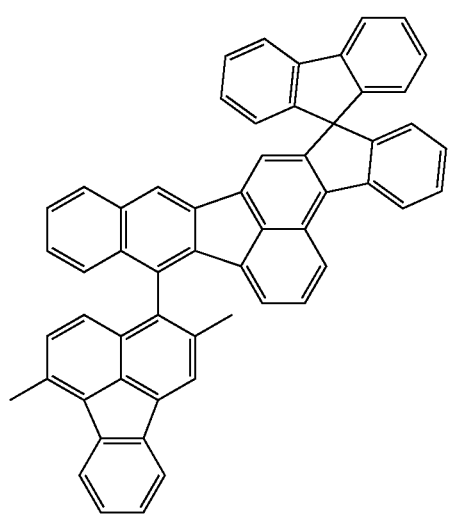
A9
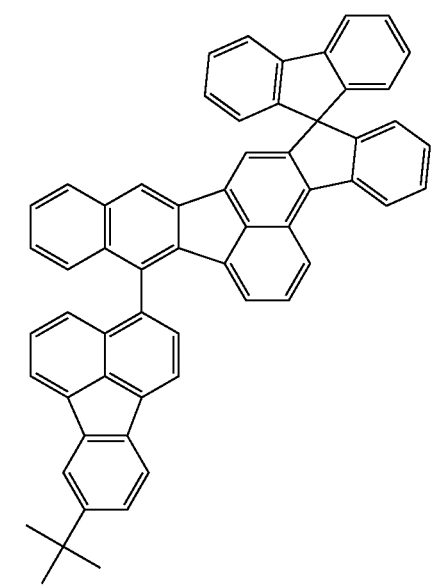
A10
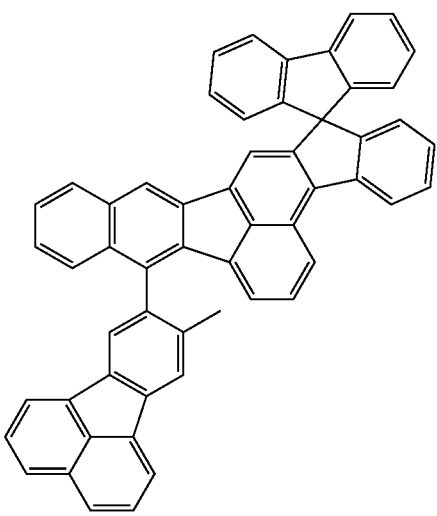
A11
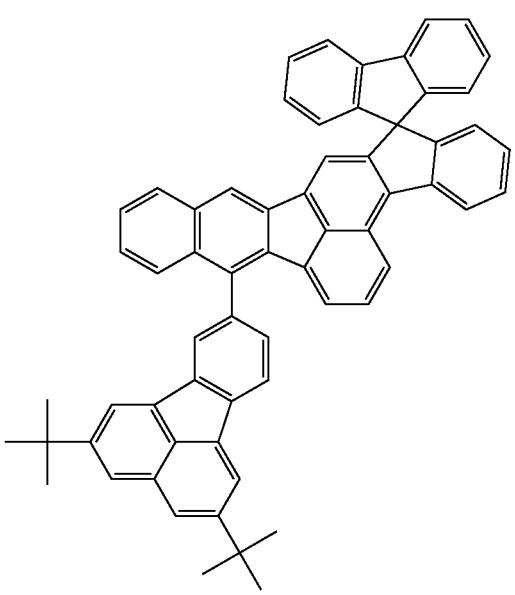

A12
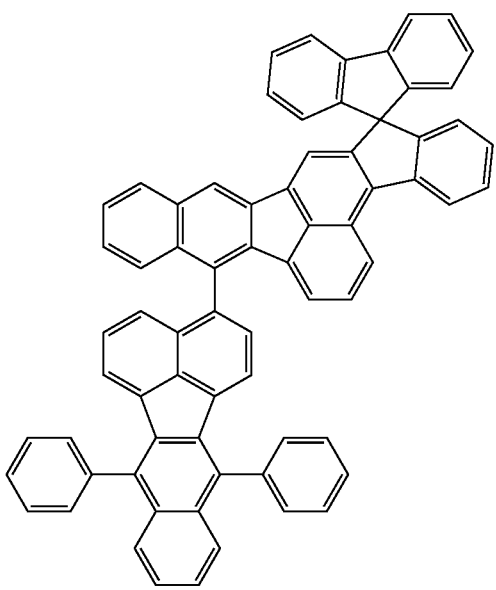
A13
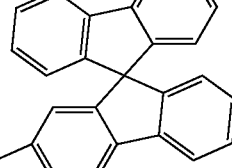
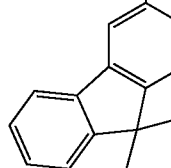
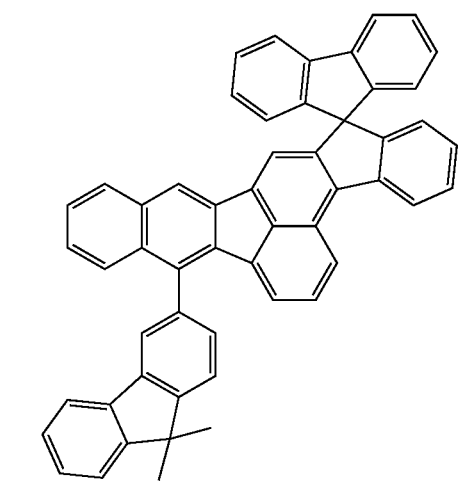
A14
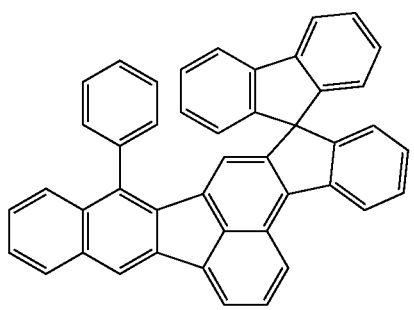
A15
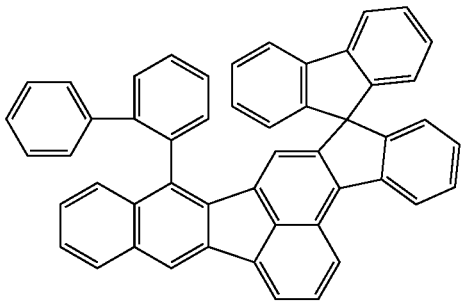
A16
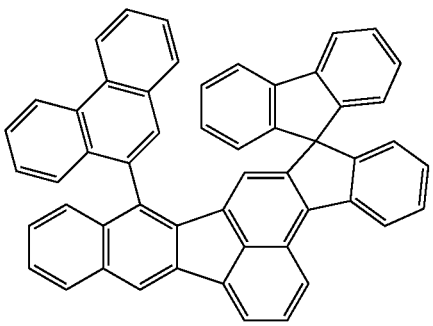
[Chem. 9]
A17
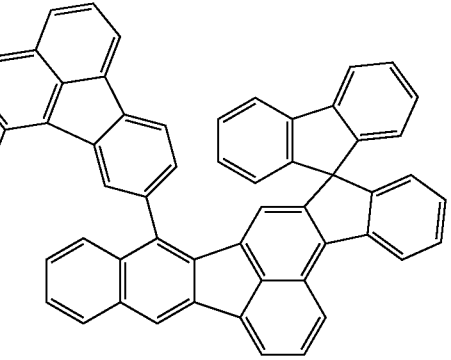
A18
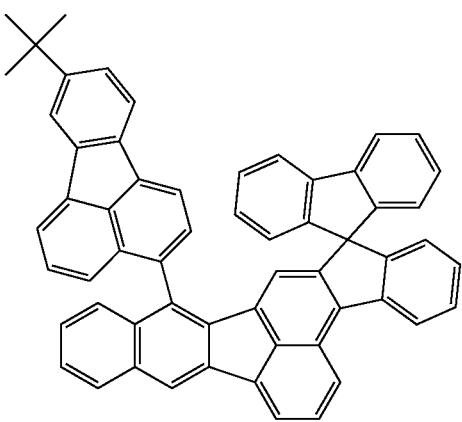

A19
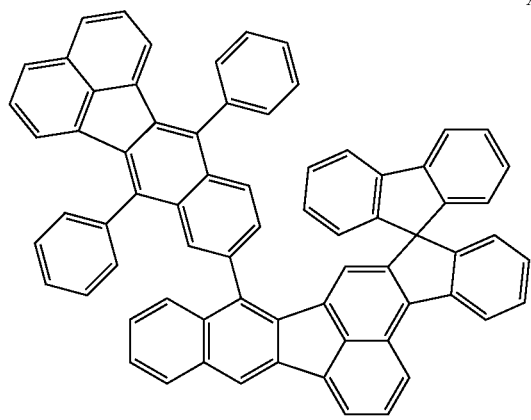
B1
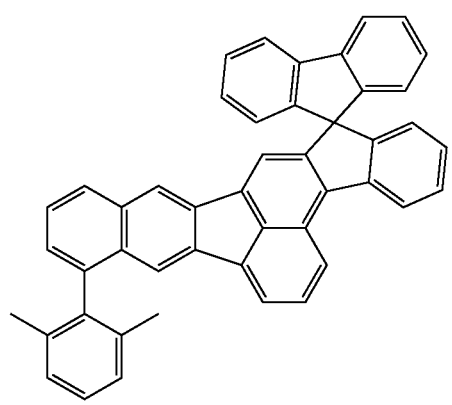
B2
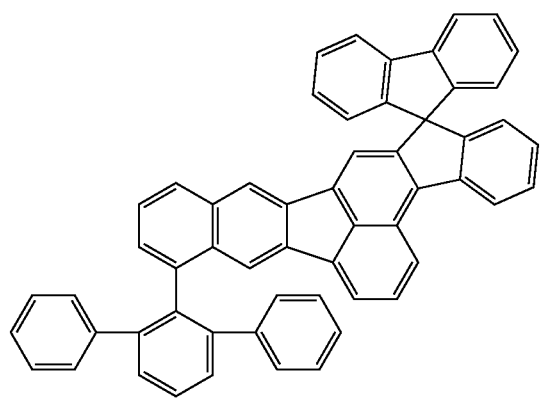
B3
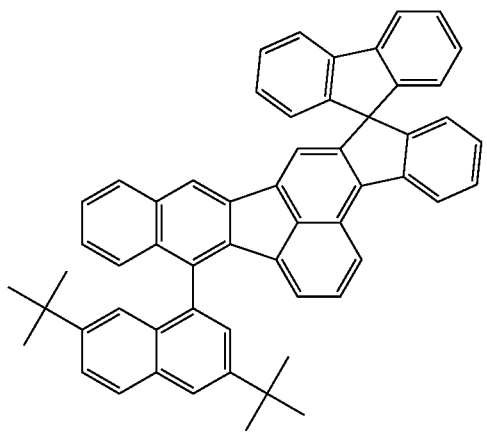
B4
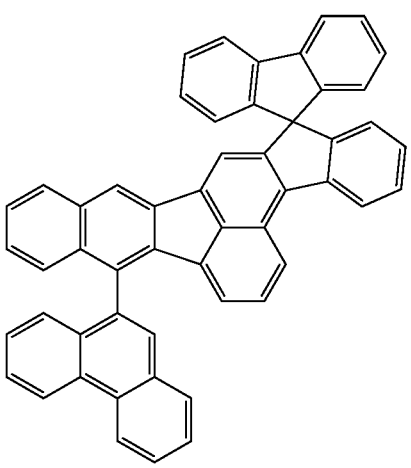
B5
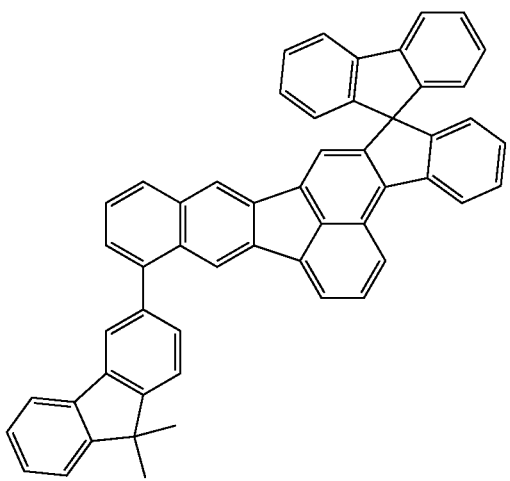

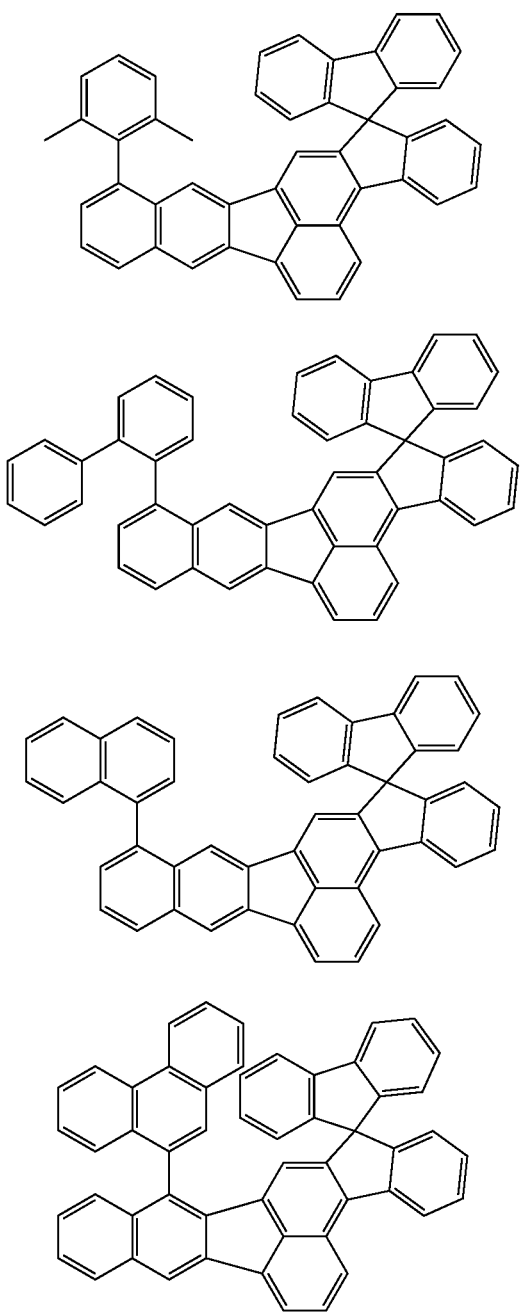
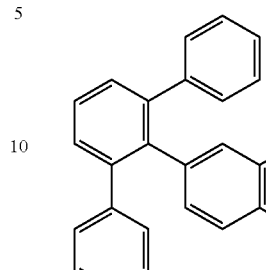
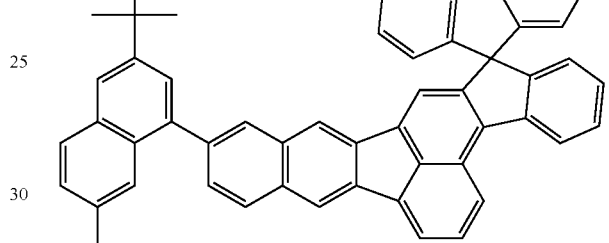
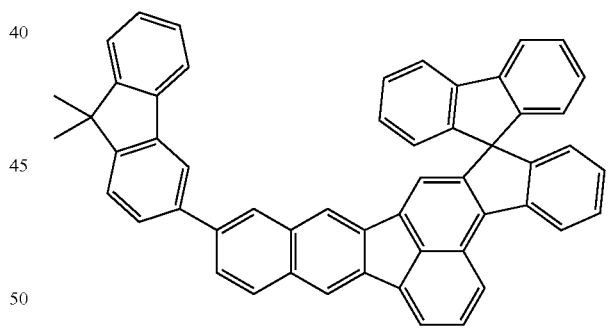
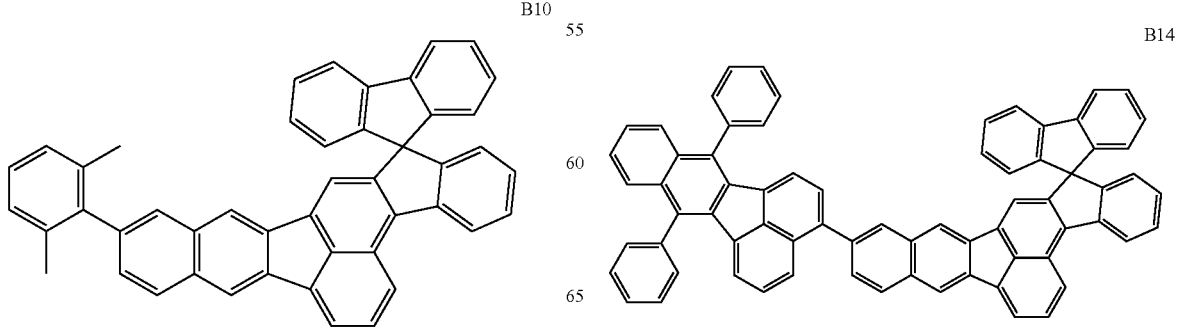
[Chem. 10]

-continued
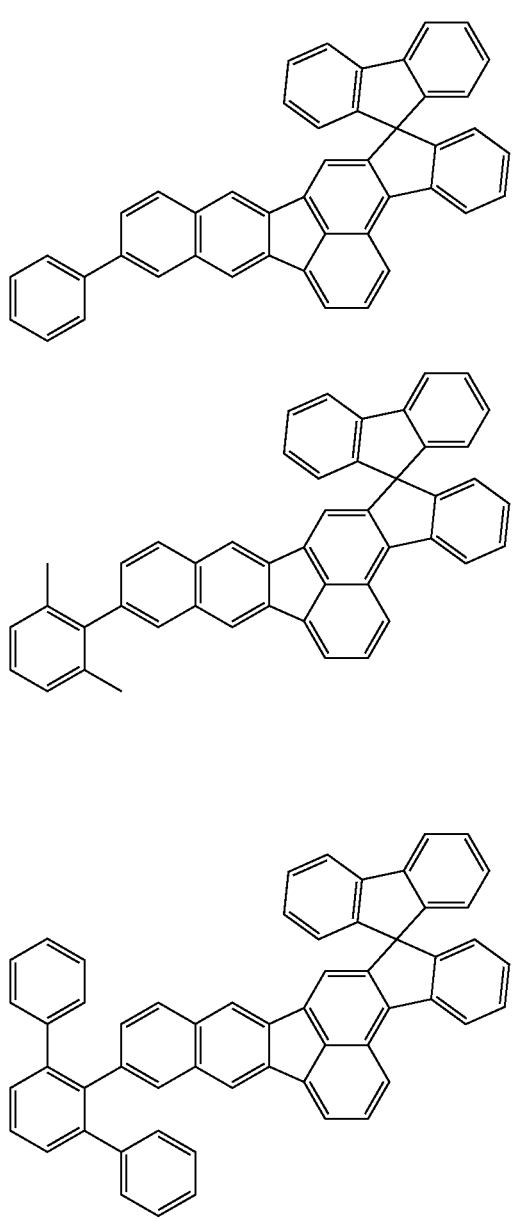
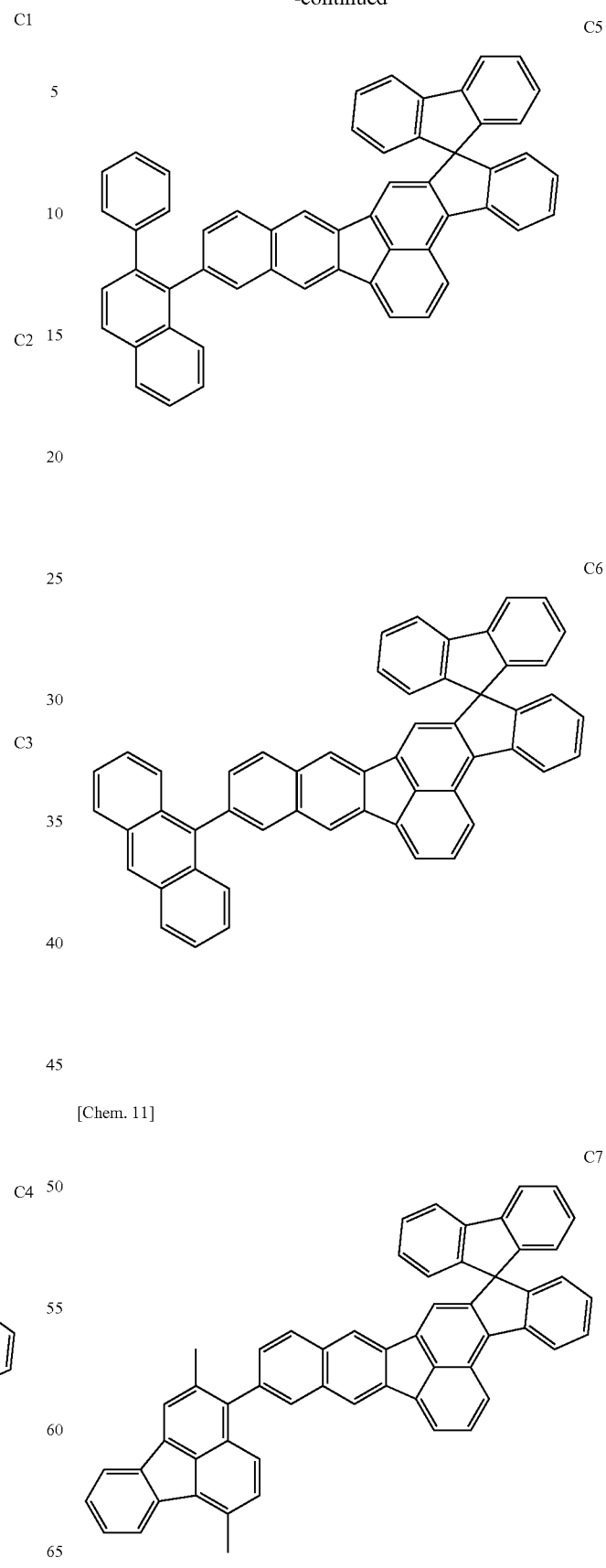
[Chem. 11]

C8
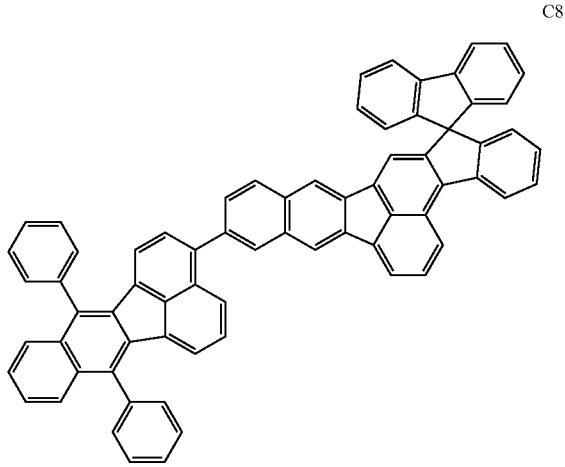
C9
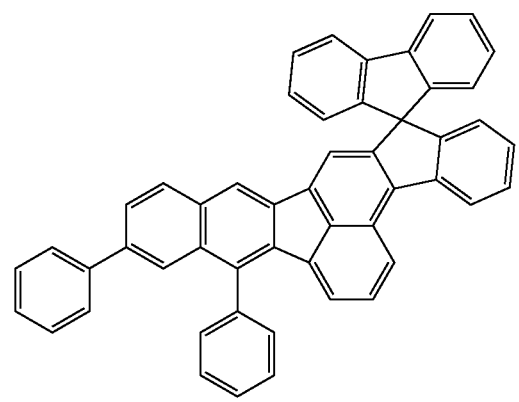
C10
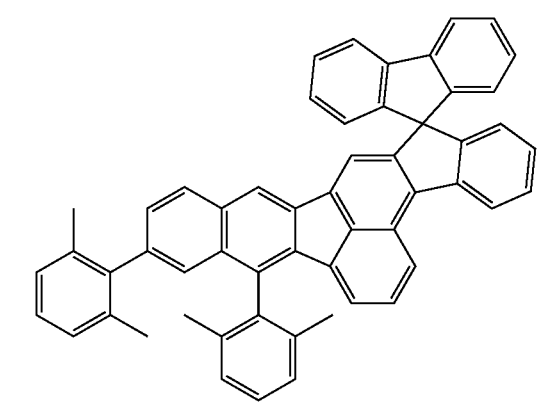
C11
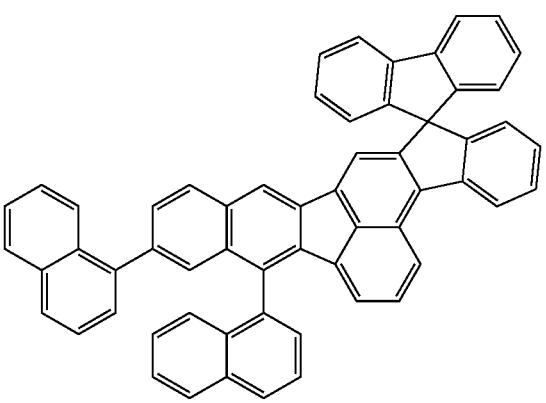
C12
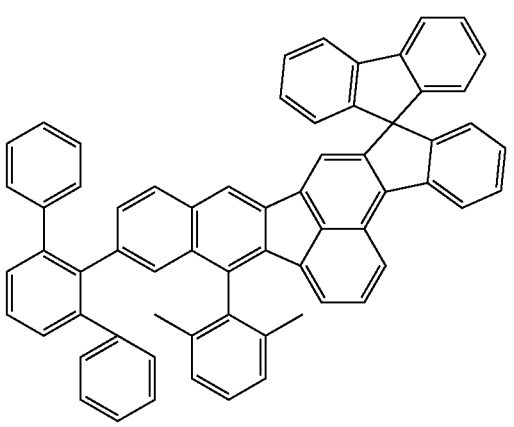
C13
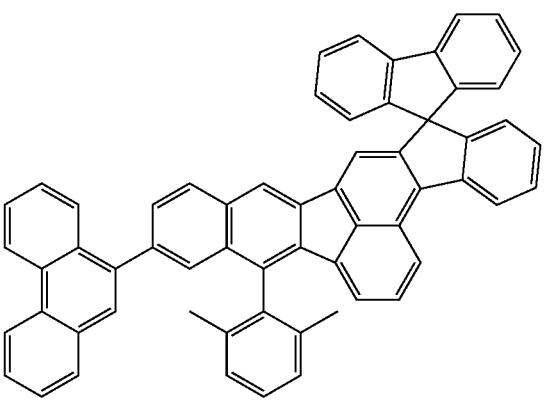
C14
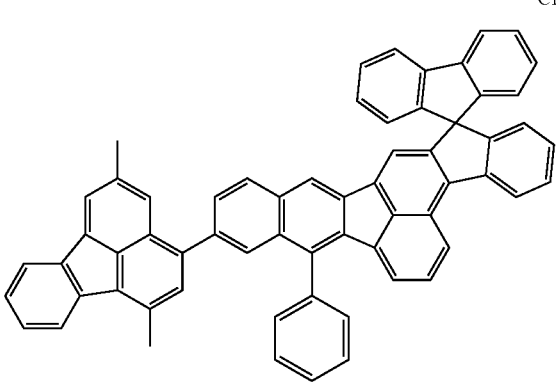

-continued

C15

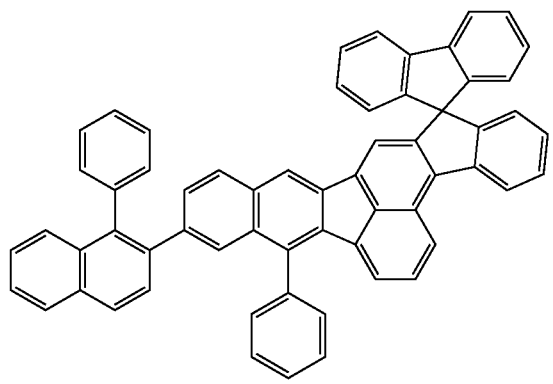

C16

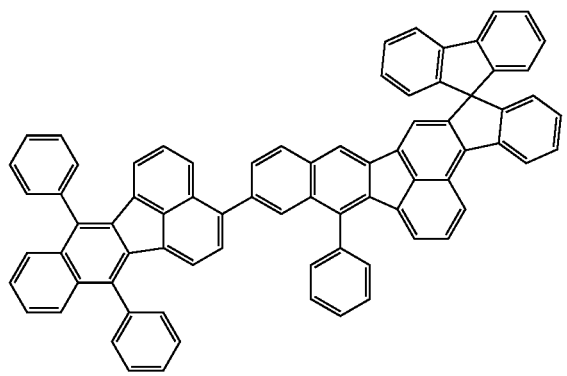

These exemplary compounds have the basic backbones thereof substituted with an aryl group. Although not shown, the basic backbone may be substituted with an alkyl group if necessary.

Properties of Exemplary Compounds

A substituent introduced perpendicularly to the basic backbone makes the structure more steric to inhibit molecular stacking, thus inhibiting concentration quenching.

This applies to all exemplary compounds other than A1 and C1.

These compounds have an aryl group introduced at the position of $R_1$ or $R_6$ in general formula 1 so that molecular stacking can be inhibited, although the effect varies from position to position.

[Chem. 12]

General formula 1

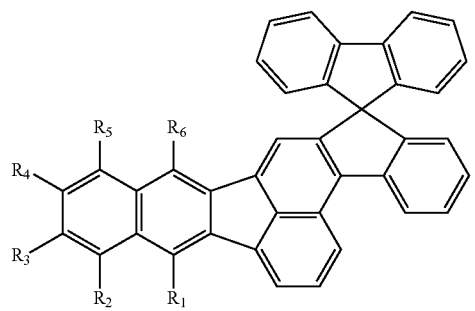

In general formula 1, the effect of inhibiting molecular stacking is greater in the following order: $R_1$, $R_6$>$R_2$, $R_4$, $R_5$>$R_3$. That is, a substituent introduced at the position of $R_1$ or $R_6$ has the greatest effect of inhibiting concentration quenching.

In view of adjustment of emission wavelength, the wavelength is longer in the following order: $R_1$, $R_6$<$R_2$, $R_4$, $R_5$<$R_3$. That is, a substituent introduced at the position of $R_3$ forms a compound having the longest emission wavelength. Thus, the emission wavelength can be finely adjusted by changing the type and position of substituent introduced.

In particular, an organic compound represented by general formula 2 below can be used. These positions, as described above, can be substituted without substantially affecting the emission wavelength and have a great effect of inhibiting molecular stacking.

[Chem. 13]

General formula 2

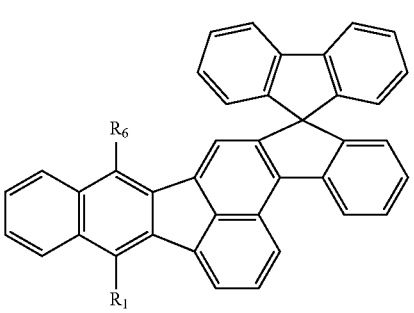

In general formula 2, $R_1$ and $R_6$ are each independently a hydrogen atom, an alkyl group, or an aryl group. The alkyl group and the aryl group are optionally substituted.

The alkyl group is methyl, ethyl, n-propyl, isopropyl, n-butyl, isobutyl, sec-butyl, or tert-butyl.

The aryl group is phenyl, biphenyl, or terphenyl.

The aryl group is optionally substituted with methyl, ethyl, n-propyl, isopropyl, n-butyl, isobutyl, sec-butyl, or tert-butyl.

The aryl group has the effect of inhibiting molecular aggregation and concentration quenching because it is attached nearly perpendicularly to the basic backbone. Although an alkyl group has a similar effect, an aryl group is more effective.

The aryl groups shown above, namely, phenyl, biphenyl, and terphenyl, have a great effect of inhibiting concentration quenching due to their bulkiness and have less tendency to make the emission wavelength longer because they hardly affect the conjugation length of the molecule.

Although an aryl group bulkier than terphenyl provides a similar effect, the effect is not greater than that of terphenyl because it has a larger molecular structure and is therefore more distant from the basic backbone.

An aryl group having an alkyl group is bulkier and therefore provides a greater effect of concentration quenching.

Group A is a group of compounds having a substituent introduced at the position of $R_1$ or $R_6$ except for A1 and has the greatest effects of concentration quenching. Among the compounds according to the present invention, these compounds emit light having shorter wavelengths. Of Group A, particularly, the compounds substituted with phenyl, biphenyl, or terphenyl can be used because they inhibit molecular aggregation while hardly affecting the emission wavelength.

Group B is a group of compounds having a substituent introduced at the position of $R_2$, $R_4$, or $R_5$ and emits light having wavelengths longer than those of Group A and shorter than those of Group C. Of Group B, particularly, the compounds having naphthyl, biphenyl, or phenanthrenyl can be used because they increase the conjugation length to vary the emission wavelength.

Group C is a group of compounds having a substituent introduced at the position of $R_3$ and emits light having the longest wavelengths. In particular, the exemplary compounds C9 to C16 emit light having longer wavelengths and have greater effects of inhibiting concentration quenching because they also have a substituent introduced at the position of R. Of these, particularly, the compounds having fluoranthenyl, benzofluoranthenyl, or phenanthrenyl can be used because they largely vary the emission wavelength.

Thus, the exemplary compounds are shown as Groups A to C. These compounds emit blue light only with the basic backbones thereof. In addition, the basic backbones of the compounds according to the present invention can be substituted to emit light longer in wavelength than blue light, for example, green light. In addition, the organic compound represented by general formula 1 can be used not only as a guest material for an organic light-emitting device, but also as a host material for an organic light-emitting device or, for example, for an electron transport layer, an electron injection layer, a hole transport layer, a hole injection layer, or a hole blocking layer. In such cases, the color of light emitted by the organic light-emitting device is not limited to blue and may instead be, for example, green, red, white, or any intermediate color. The organic compound can also be used as a host material for a light-emitting layer of an organic light-emitting device that emits green light.

Description of Synthesis Route

An example of the synthesis route of the organic compound according to the present invention will now be described. The reaction formula is shown below.

An intermediate D2 can be synthesized by, for example, reacting a halide D1 with 4,4,5,5-tetramethyl-[1,3,2]dioxaborane in toluene in the presence of triethylamine and Pd(dppp)Cl$_2$, which serves as a catalyst.

An intermediate D5 or D6 can be synthesized by, for example, reacting the pinacolboronate D2 with a corresponding halide D3 or D4 in a mixture of toluene, ethanol, and distilled water in the presence of sodium carbonate and Pd(PPh$_3$)$_4$, which serves as a catalyst.

An intermediate D7 can be synthesized by, for example, reacting the intermediate D5 with trifluoromethanesulfonic anhydride in pyridine.

An organic compound D8 represented by general formula 1 can be synthesized by, for example, reacting the intermediate D6 or D7 in DMF in the presence of DBU, LiCl, and Pd(PPh$_3$)$_2$Cl$_2$, which serves as a catalyst.

[Chem. 14]

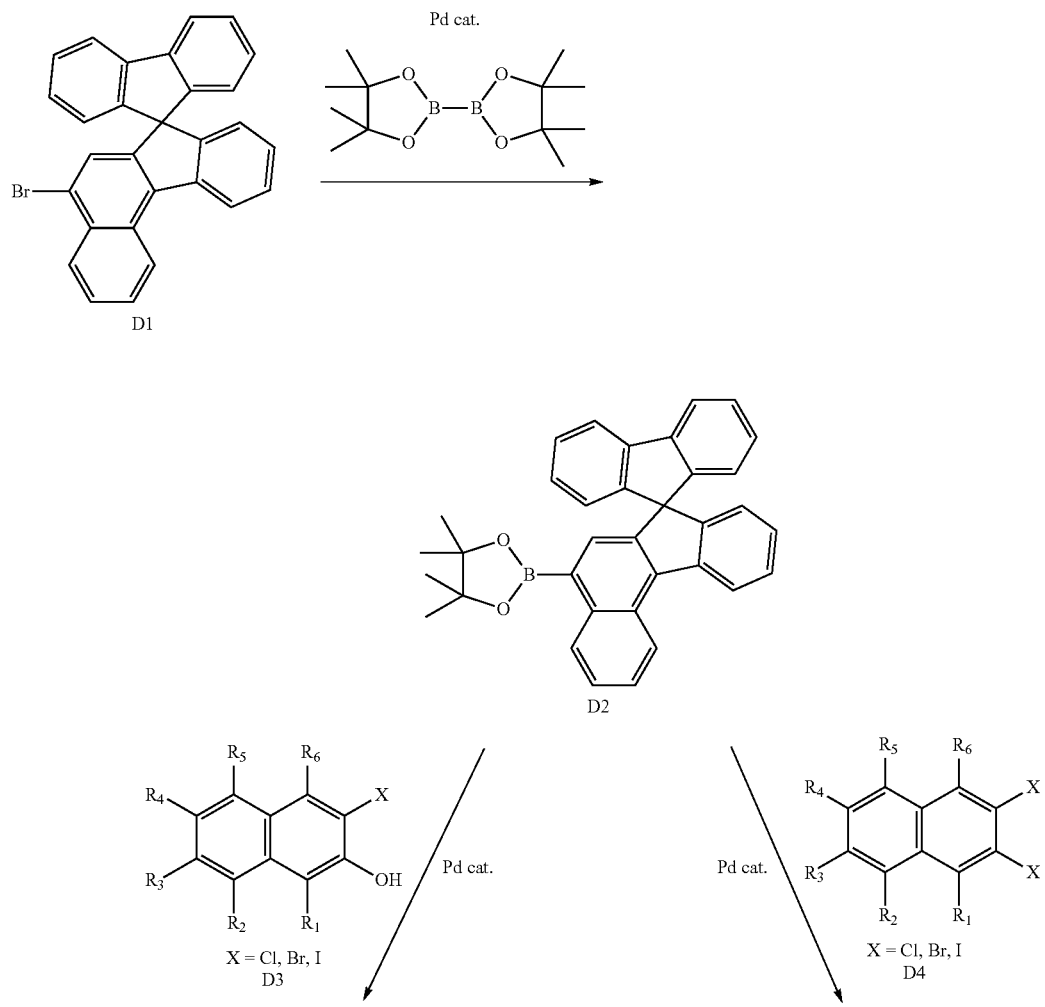

-continued
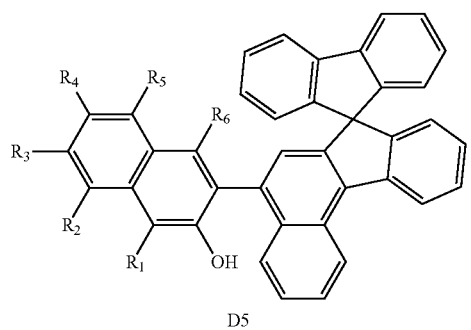
D5
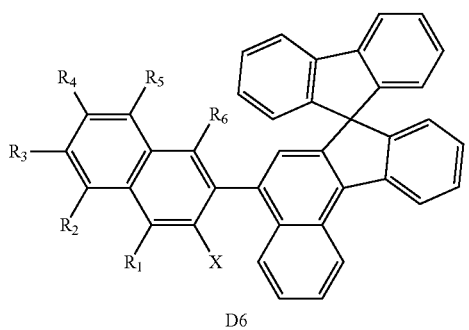
D6
Tf₂O ↓
Pd cat. DBU ↓
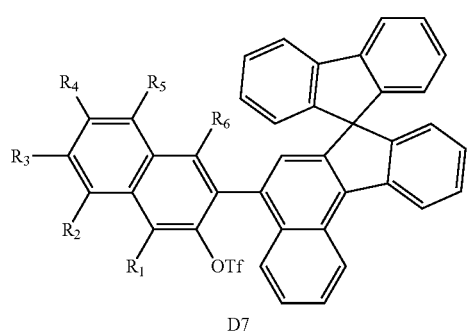
D7
Pd cat. DBU →
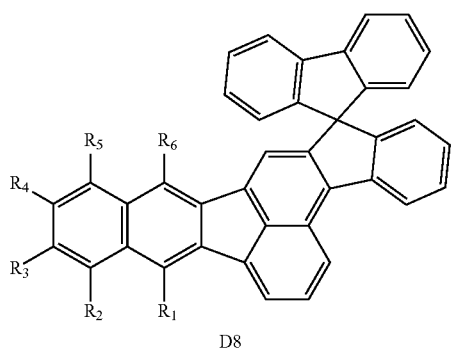
D8
Other Organic Compounds and Materials Thereof
Various organic compounds can be synthesized by changing D3 or D4 in the above reaction formula. Table 2 shows examples of synthesized compounds.
TABLE 2
| Example No. | D3 or D4 | Synthesized compound | Exemplary compound |
|---|---|---|---|
| 1 | ![structure] | ![structure] | A2 |

TABLE 2-continued
| Example No. | D3 or D4 | Synthesized compound | Exemplary compound |
|---|---|---|---|
| 2 | 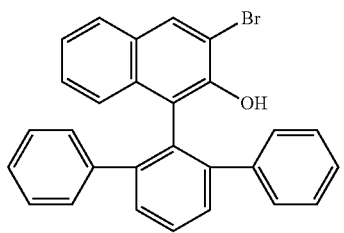 [SMILES: Oc1c(Br)cc2ccccc2c1-c1c(-c2ccccc2)cccc1-c1ccccc1] | 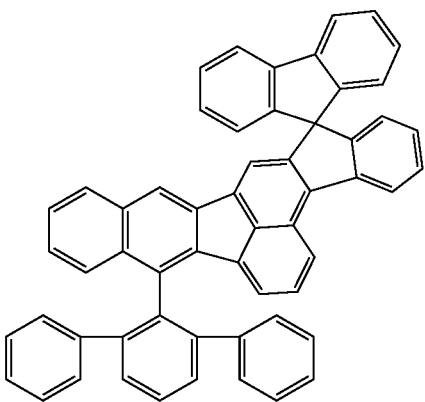 [SMILES: c1ccc(-c2cccc(-c3ccccc3)c2-c2c3c(cc4ccccc24)-c2cc4c(c5cccc-3c25)-c2ccccc2C42c3ccccc3-c3ccccc32)cc1] | A4 |
| 3 | 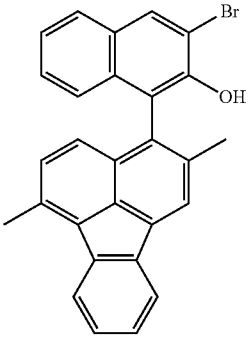 | 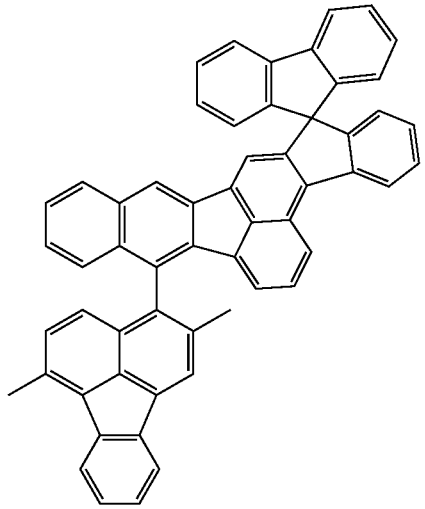 [SMILES: Cc1cc2c3c(c(C)ccc3c1-c1c3c(cc4ccccc14)-c1cc4c(c5cccc-3c15)-c1ccccc1C41c3ccccc3-c3ccccc31)-c1ccccc1-2] | A8 |
| 4 | 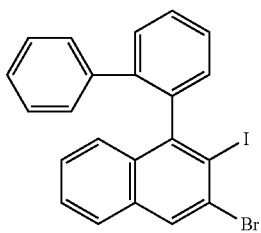 [SMILES: Brc1cc2ccccc2c(-c2ccccc2-c2ccccc2)c1I] | 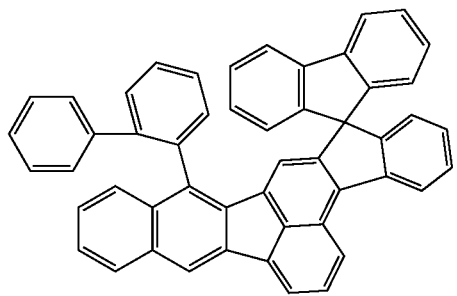 [SMILES: c1ccc(-c2ccccc2-c2c3c(cc4ccccc24)-c2cccc4c5c(cc-3c24)C2(c3ccccc3-c3ccccc32)c2ccccc2-5)cc1] | A15 |

TABLE 2-continued

| Example No. | D3 or D4 | Synthesized compound | Exemplary compound |
|---|---|---|---|
| 5 | | | B1 |
| 6 | | | B12 |
| 7 | | | C12 |

An example of the synthesis route of the intermediate D1 will now be described. The reaction formula is shown below.

An intermediate D11 can be synthesized by, for example, reacting D9 with D10 in a mixture of toluene, ethanol, and distilled water in the presence of sodium carbonate and Pd(PPh$_3$)$_4$, which serves as a catalyst.

An intermediate D13 can be synthesized by, for example, lithiating D11 with n-butyllithium in tetrahydrofuran, reacting the product with D12, roughly purifying the product, and heating and stirring the product in acid.

The intermediate D1 can be synthesized by reacting D13 with bromine in carbon tetrachloride.

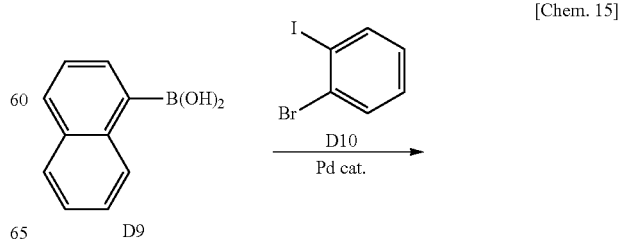

[Chem. 15]

-continued

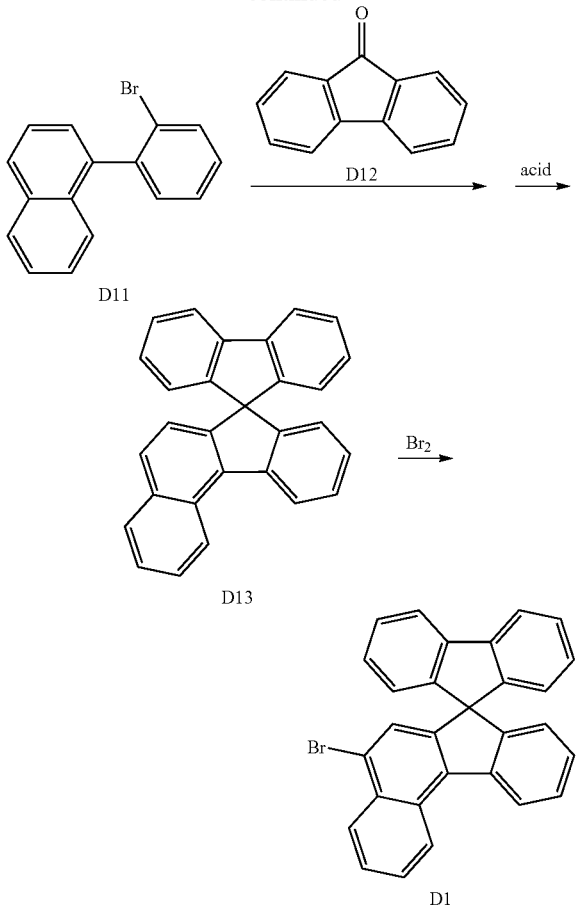

Description of Organic Light-Emitting Device

Next, an organic light-emitting device according to an embodiment of the present invention will be described.

The organic light-emitting device according to this embodiment includes a pair of electrodes, namely, an anode and a cathode, and an organic compound layer disposed therebetween. The organic compound layer contains an organic compound represented by general formula 1.

In the organic light-emitting device according to this embodiment, the organic compound layer may include a plurality of layers such as a hole injection layer, a hole transport layer, a light-emitting layer, a hole blocking layer, an exciton blocking layer, an electron transport layer, and an electron injection layer. These layers can be used in any combination.

If the organic compound according to this embodiment is used as a guest material, the concentration of the guest material in the host material is preferably 0.1% to 30% by mass, more preferably 0.5% to 10% by mass.

As a result of various studies, the present inventors have found that a device formed using an organic compound of the present invention represented by general formula 1 above as a host or guest material of a light-emitting layer, particularly, as a guest material, provides optical output with high efficiency and high luminance and has extremely high durability.

In addition to the organic compound according to the present invention, other materials can be used in combination for the organic light-emitting device according to this embodiment as needed, including a known low-molecular-weight or polymer hole injection material or hole transport material, a known low-molecular-weight or polymer host material or guest material, and a known low-molecular-weight or polymer electron injection material or electron transport material.

Examples of such compounds are shown below.

The hole injection or transport material used can be a material having high hole mobility. Example of low-molecular-weight or polymer materials with hole injection or transport properties include, but are not limited to, triarylamines, phenylenediamines, stilbenes, phthalocyanines, porphyrins, polyvinylcarbazole, polythiophene, and other conductive polymers.

Table 3 shows specific structural formulae of host materials. As the host material, derivatives of the compounds represented by the structural formulae shown in Table 3 can also be used. Other examples include, but are not limited to, fused ring compounds (such as fluorenes, naphthalenes, anthracenes, pyrenes, carbazoles, quinoxalines, and quinolines), organoaluminum complexes such as tris(8-quinolinolato)aluminum, organozinc complexes, and polymers such as triphenylamines, polyfluorenes, and polyphenylenes.

TABLE 3

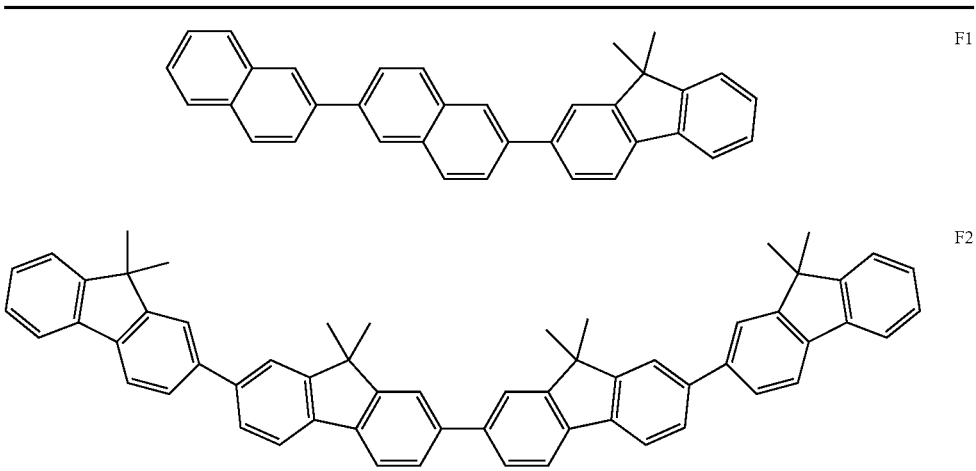

TABLE 3-continued
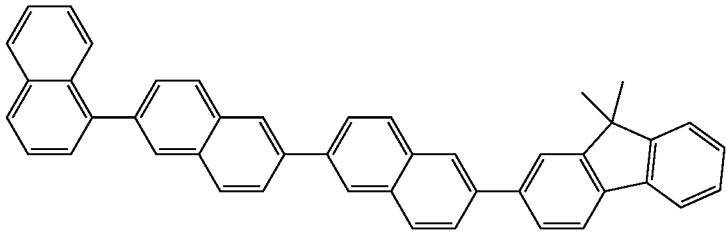 [SMILES: CC1(C)c2ccccc2-c2ccc(-c3ccc4cc(-c5ccc6cc(-c7cccc8ccccc78)ccc6c5)ccc4c3)cc21]
F3
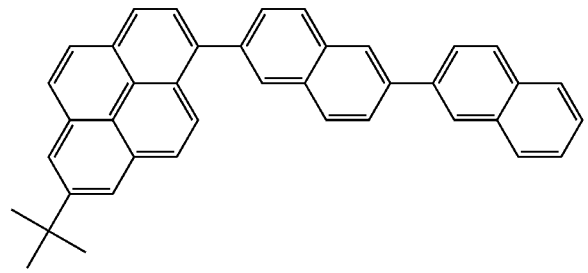 [SMILES: CC(C)(C)c1cc2ccc3ccc(-c4ccc5cc(-c6ccc7ccccc7c6)ccc5c4)c4ccc(c1)c2c34]
F4
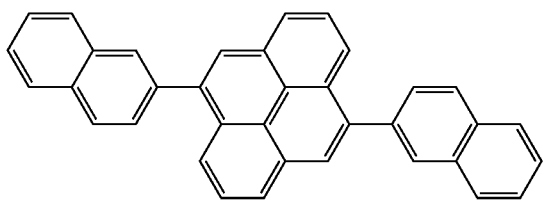 [SMILES: c1ccc2cc(-c3cc4cccc5c(-c6ccc7ccccc7c6)cc6cccc3c6c45)ccc2c1]
F5
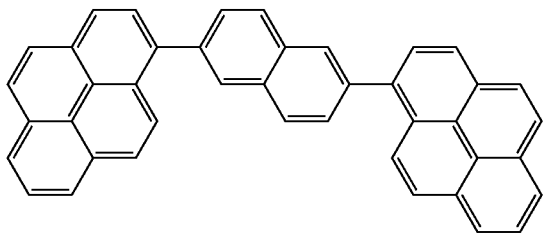 [SMILES: c1cc2ccc3ccc(-c4ccc5cc(-c6ccc7ccc8cccc9ccc6c7c89)ccc5c4)c4ccc(c1)c2c34]
F6
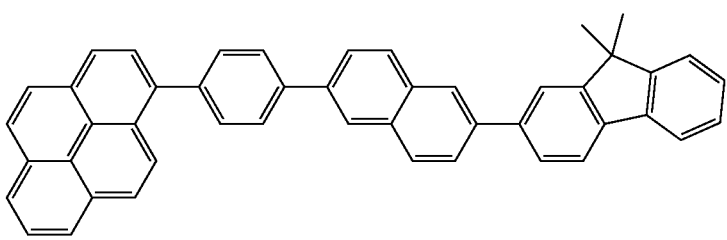 [SMILES: CC1(C)c2ccccc2-c2ccc(-c3ccc4cc(-c5ccc(-c6ccc7ccc8cccc9ccc6c7c89)cc5)ccc4c3)cc21]
F7
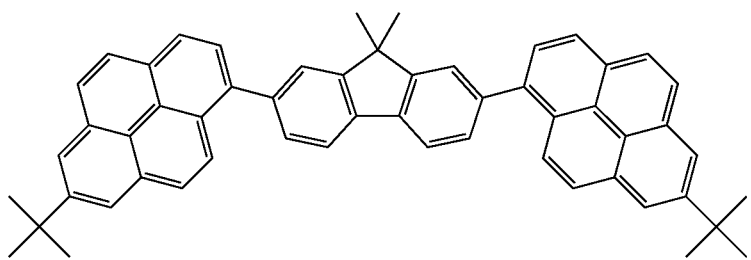 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
F8

TABLE 3-continued
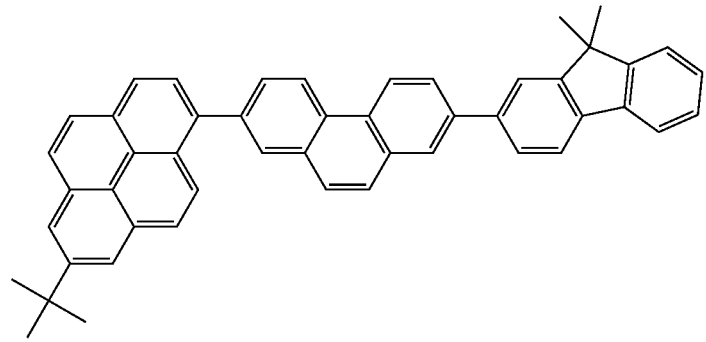 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34]
F9
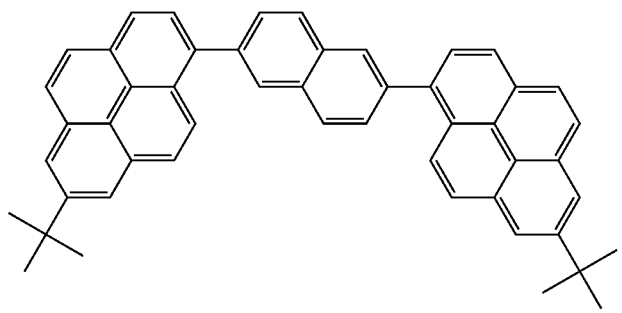 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]
F10
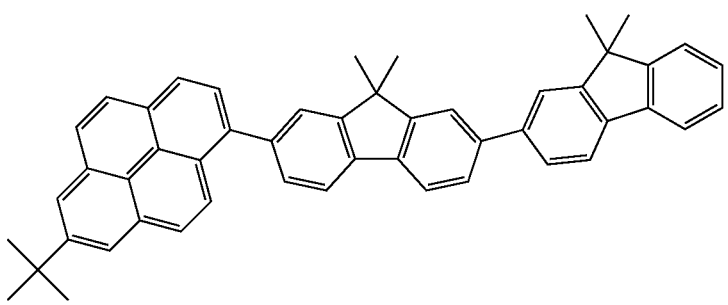 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34]
F11
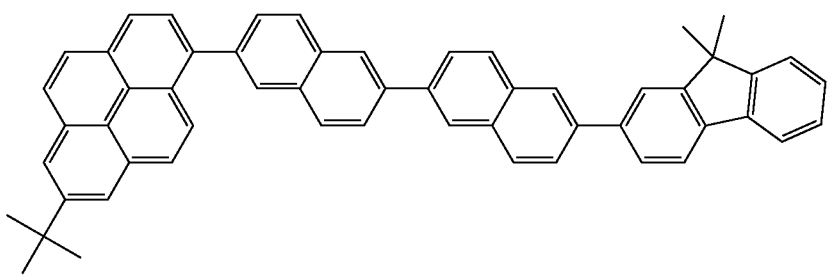 [SMILES: CC(C)(C)c1cc2ccc3ccc(-c4ccc5cc(-c6ccc7cc(-c8ccc9c(c8)C(C)(C)c8ccccc8-9)ccc7c6)ccc5c4)c4ccc(c1)c2c34]
F12
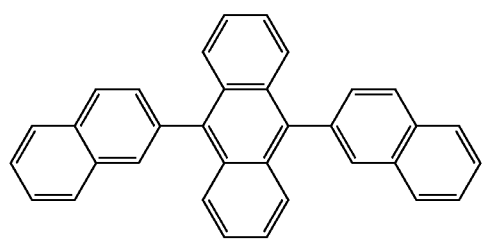 [SMILES: c1ccc2cc(-c3c4ccccc4c(-c4ccc5ccccc5c4)c4ccccc34)ccc2c1]
F13

TABLE 3-continued
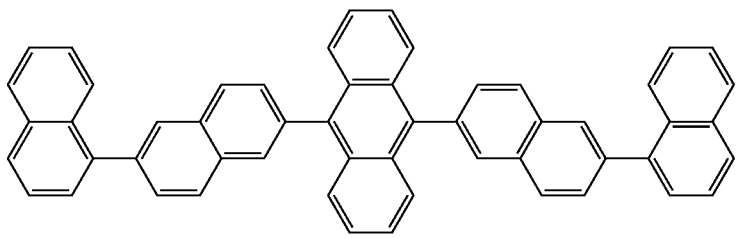 [SMILES: c1ccc2c(-c3ccc4cc(-c5c6ccccc6c(-c6ccc7cc(-c8cccc9ccccc89)ccc7c6)c6ccccc56)ccc4c3)cccc2c1] F14
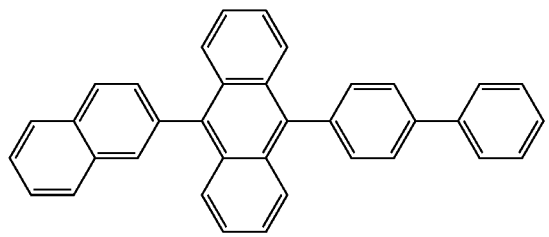 [SMILES: c1ccc(-c2ccc(-c3c4ccccc4c(-c4ccc5ccccc5c4)c4ccccc34)cc2)cc1] F15
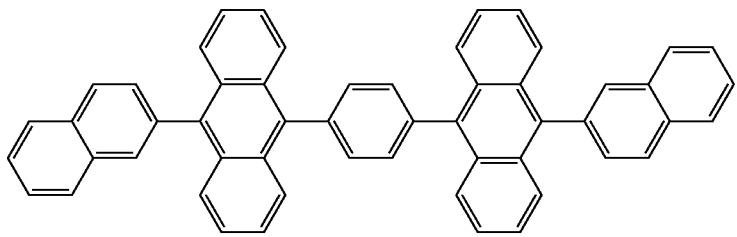 [SMILES: c1ccc2cc(-c3c4ccccc4c(-c4ccc(-c5c6ccccc6c(-c6ccc7ccccc7c6)c6ccccc56)cc4)c4ccccc34)ccc2c1] F16
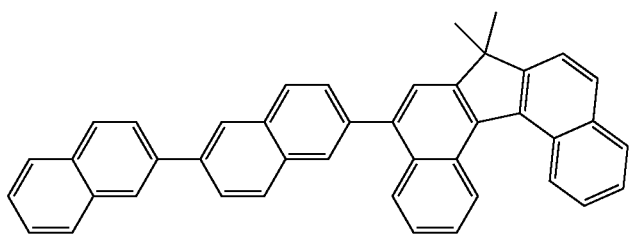 [SMILES: CC1(C)c2ccc3ccccc3c2-c2c1cc(-c1ccc3cc(-c4ccc5ccccc5c4)ccc3c1)c1ccccc21] F17
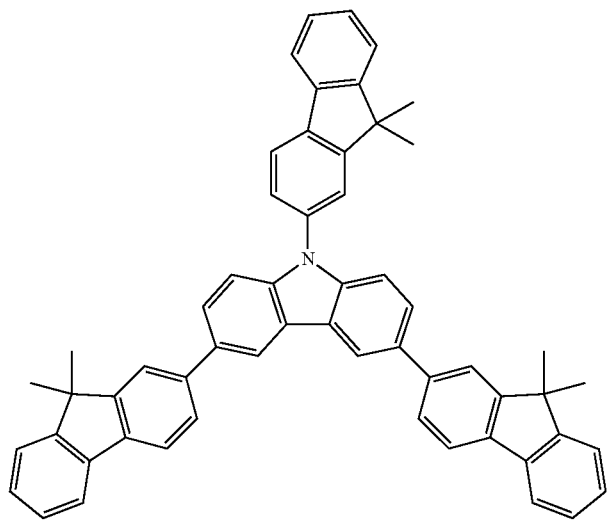 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21] F18

TABLE 3-continued
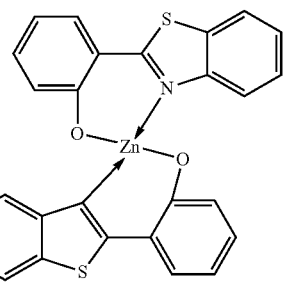
F19
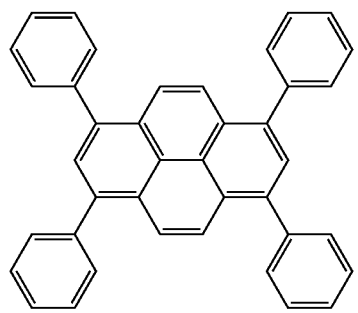 [SMILES: c1ccc(-c2cc(-c3ccccc3)c3ccc4c(-c5ccccc5)cc(-c5ccccc5)c5ccc2c3c54)cc1]
F20
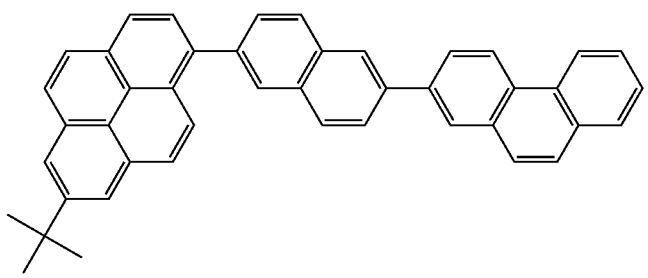 [SMILES: CC(C)(C)c1cc2ccc3ccc(-c4ccc5cc(-c6ccc7c(ccc8ccccc87)c6)ccc5c4)c4ccc(c1)c2c34]
F21
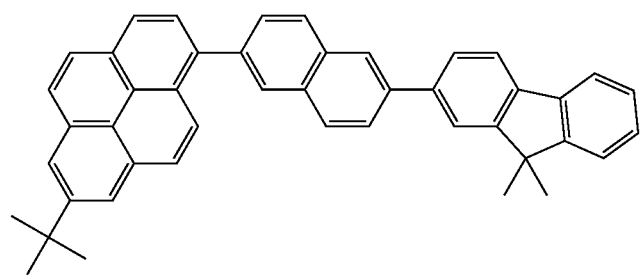 [SMILES: CC(C)(C)c1cc2ccc3ccc(-c4ccc5cc(-c6ccc7c(c6)C(C)(C)c6ccccc6-7)ccc5c4)c4ccc(c1)c2c34]
F22
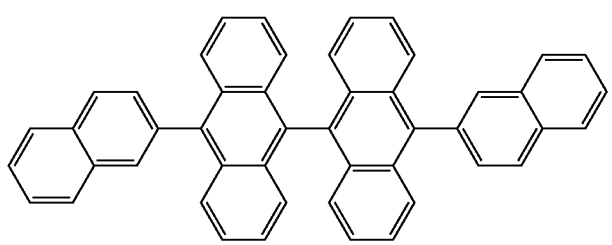 [SMILES: c1ccc2cc(-c3c4ccccc4c(-c4c5ccccc5c(-c5ccc6ccccc6c5)c5ccccc45)c4ccccc34)ccc2c1]
F23
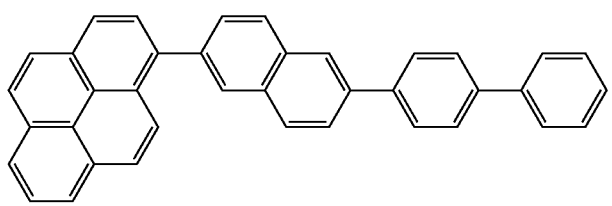 [SMILES: c1ccc(-c2ccc(-c3ccc4cc(-c5ccc6ccc7cccc8ccc5c6c78)ccc4c3)cc2)cc1]
F24

TABLE 3-continued

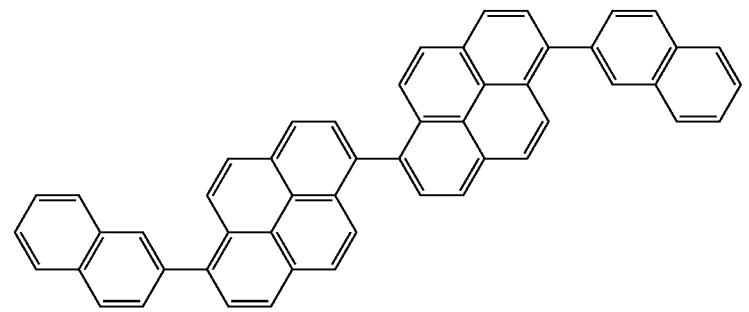 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1]
F25

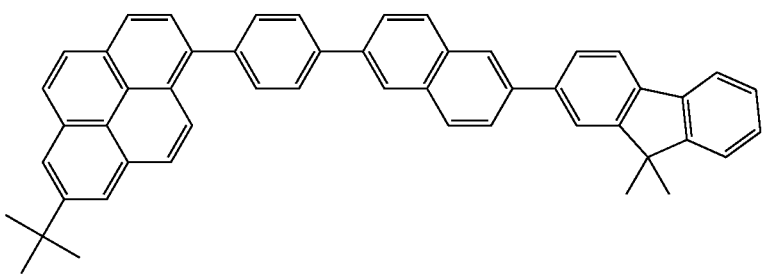 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34]
F26

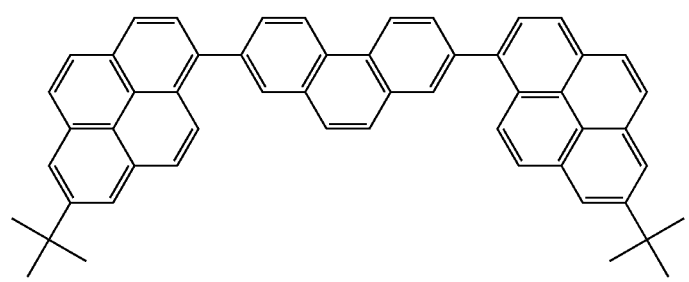 [SMILES: CC(C)(C)c1cc2ccc3ccc(-c4ccc5c(ccc6cc(-c7ccc8ccc9cc(C(C)(C)C)cc%10ccc7c8c9%10)ccc65)c4)c4ccc(c1)c2c34]
F27

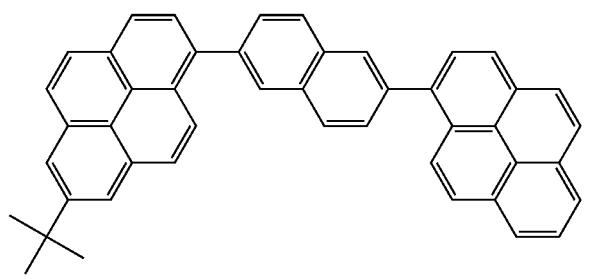 [SMILES: CC(C)(C)c1cc2ccc3ccc(-c4ccc5cc(-c6ccc7ccc8cccc9ccc6c7c89)ccc5c4)c4ccc(c1)c2c34]
F28

The electron injection or transport material used is selected taking into account, for example, the balance against the hole mobility of the hole injection or transport material. Examples of materials with electron injection or transport properties include, but are not limited to, oxadiazoles, oxazoles, pyrazines, triazoles, triazines, quinolines, quinoxalines, phenanthrolines, and organoaluminum complexes.

As the anode material, a material having a higher work function can be used. Examples of such materials include metals such as gold, platinum, silver, copper, nickel, palladium, cobalt, selenium, vanadium, and tungsten; alloys thereof; and metal oxides such as tin oxide, zinc oxide, indium oxide, indium tin oxide (ITO), and indium zinc oxide. In addition, conductive polymers such as polyaniline, polypyrrole, and polythiophene can be used. These electrode materials may be used alone or in combination. In addition, the anode may have a monolayer structure or a multilayer structure.

As the cathode material, on the other hand, a material having a lower work function can be used. Examples of such materials include alkali metals such as lithium; alkaline earth metals such as calcium; and metals such as aluminum, titanium, manganese, silver, lead, and chromium. In addition, alloys of these metals can be used, including magnesium-silver, aluminum-lithium, and aluminum-magnesium. Metal oxides such as ITO can also be used. These electrode materials may be used alone or in combination. In addition, the cathode may have a monolayer structure or a multilayer structure.

In the organic light-emitting device according to this embodiment, the layer containing the organic compound according to this embodiment and the other organic compound layers are typically formed by vacuum evaporation, ion-assisted deposition, sputtering, plasma deposition, or a known coating process using an appropriate solvent (such as spin coating, dipping, casting, the Langmuir-Blodgett (LB)

technique, and inkjet coating). For example, if the layers are formed by vacuum evaporation or solution coating, they have superior stability over time because they are less likely to crystallize. In addition, if the layers are formed by coating, films can be formed in combination with an appropriate binder resin.

Examples of the binder resin include, but are not limited to, polyvinylcarbazole resins, polycarbonate resins, polyester resins, acrylonitrile-butadiene-styrene (ABS) resins, acrylic resins, polyimide resins, phenolic resins, epoxy resins, silicone resins, and urea resins. These binder resins may be used alone as a homopolymer or copolymer or may be used as a mixture of two or more. In addition, additives such as known plasticizers, antioxidants, and ultraviolet absorbers may be used in combination as needed.

Applications of Organic Light-Emitting Device

The organic light-emitting device according to this embodiment can be used for a display apparatus or an illumination apparatus. Other applications include exposure light sources for electrophotographic image-forming apparatuses and backlights for liquid-crystal display apparatuses.

The display apparatus includes a display unit including organic light-emitting devices according to this embodiment. The display unit has a plurality of pixels. The pixels include the organic light-emitting devices according to this embodiment and thin-film transistors (TFT) as an example of switching devices for controlling the luminous intensities thereof. The anodes or cathodes of the organic light-emitting devices are connected to the drains or sources of the TFTs. The display apparatus can be used as an image display apparatus such as a personal computer.

The display apparatus may also be an image output apparatus including an image input unit configured to input information from, for example, an area charge-coupled device (CCD) sensor, a linear CCD sensor, or a memory card and a display unit configured to display the input image. In addition, the display apparatus may be used for an image pickup apparatus or an inkjet printer both as a display unit having the image output function of displaying an image on the basis of image information input from outside and as a control panel having the image input function of inputting information on the basis of which the image is processed. The display apparatus may also be used as a display unit of a multifunction printer.

Next, a display apparatus including organic light-emitting devices according to this embodiment will be described with reference to FIGURE.

FIGURE is a schematic sectional view of the organic light-emitting devices according to this embodiment and TFTs serving as an example of switching devices connected to the organic light-emitting devices. In FIGURE, two pairs of organic light-emitting devices and TFTs are illustrated. The detailed structure will now be described.

The display apparatus in FIGURE includes a substrate 1 such as a glass substrate, a moisture-proofing film 2 disposed over the substrate 1 to protect TFTs 8 and organic compound layers 12, metal gates 3, gate insulators 4, and semiconductor layers 5.

The TFTs 8 include the semiconductor layers 5, drains 6, and sources 7. An insulating film 9 is disposed over the TFTs 8. Anodes 11 of the organic light-emitting devices are connected to the sources 7 via contact holes 10. The display apparatus, however, is not limited to this structure. For example, either the anodes 11 or the cathodes 13 may be connected to either the sources 7 or the drains 6 of the TFTs 8.

In FIGURE, the organic compound layers 12, each including a plurality of organic compound layers, are shown as single layers for illustration purposes. A first protective layer 14 and a second protective layer 15 are disposed over the cathodes 13 to inhibit degradation of the organic light-emitting devices.

The type of switching devices in the display apparatus according to this embodiment is not particularly limited. For example, single-crystal silicon substrates, metal-insulator-metal (MIM) devices, or amorphous silicon (a-Si) devices may instead be used.

EXAMPLES

Example 1

Synthesis of Exemplary Compound A1

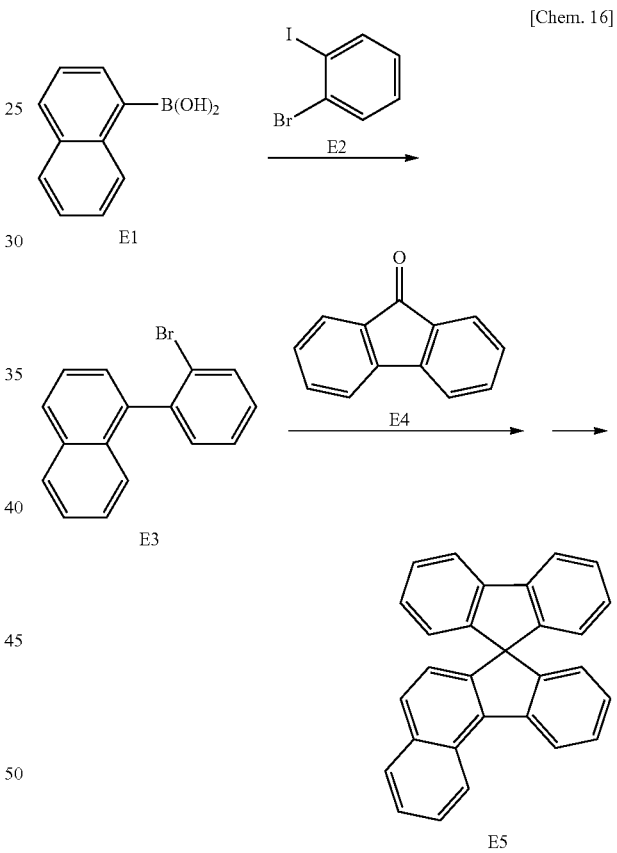

[Chem. 16]

First, 2.0 g (12 mmol) of E1 and 4.0 g (14 mmol) of E2 were put in 50 mL of toluene, 25 mL of ethanol, and 25 mL of 20% by weight aqueous sodium carbonate solution. Then, 0.32 g (0.23 mmol) of tetrakis(triphenylphosphine)palladium(0) was added, and the solution was heated to 90 degrees Celsius and was stirred for three and a half hours. After cooling, water and toluene were added, the product was extracted with toluene, and the extract was dried with sodium sulfate. After the solvent was removed, the residue was purified by silica gel column chromatography (mobile phase: chloroform and heptane in a ratio of 1:7), thus yielding 3.2 g of E3 (yield: 97%).

After 1.9 g (6.7 mmol) of E3 was dissolved in tetrahydrofuran (100 mL), the solution was cooled to −78 degrees Celsius, 4.6 mL (7.4 mmol) of n-butyllithium was gradually added dropwise, and the solution was stirred for one hour. Then, 1.5 g (8.0 mmol) of 9-fluorenone dissolved in 8.5 mL of tetrahydrofuran was gradually added dropwise at −78 degrees Celsius, and the solution was stirred for three hours while being gradually cooled to room temperature. A saturated aqueous sodium hydrogen carbonate solution was added, the product was extracted with dichloromethane, and the extract was dried with sodium sulfate. After the solvent was removed, 25 mL of acetic acid and 0.5 mL of dilute hydrochloric acid were added to the residue, and it was heated and refluxed for six hours. After cooling, water was added, and the precipitate was filtered out. The filtrate was purified by silica gel column chromatography (mobile phase: chloroform and heptane in a ratio of 1:4) and was dispersed in methanol for cleaning, thus yielding 2.0 g of E5 (yield: 81%).

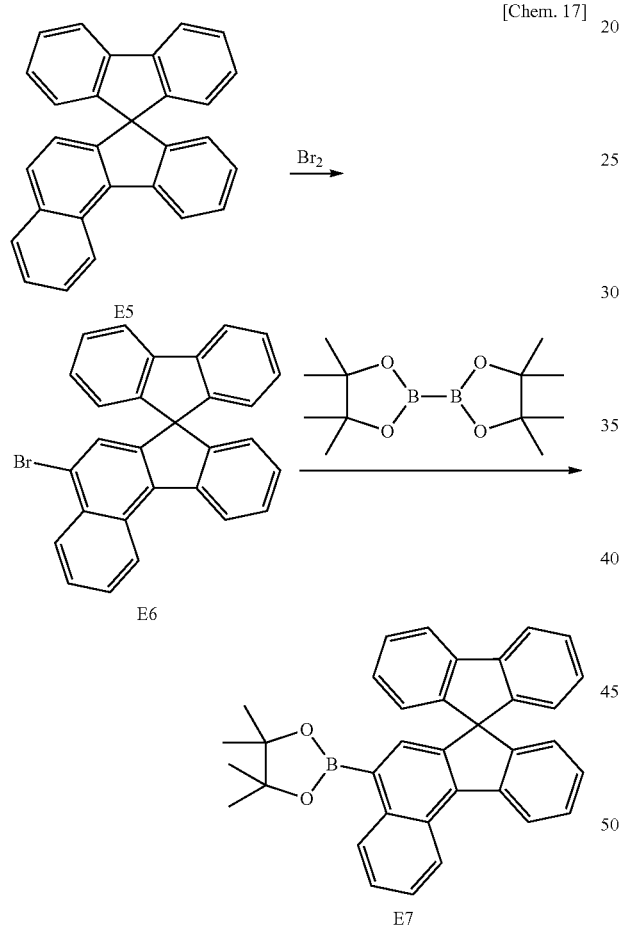

[Chem. 17]

After 1.3 g (3.5 mmol) of E5 was dissolved in 35 mL of carbon tetrachloride, 0.18 mL (7.4 mmol) of bromine was gradually added dropwise, and the solution was stirred for four hours. Then, methanol was added, the precipitate was filtered out, and the filtrate was cleaned with methanol. The filtrate was subjected to silica gel column chromatography (mobile phase: heptane) and was recrystallized with toluene and heptane, thus yielding 1.1 g of E6 (yield: 68%).

Dissolved in 20 mL of 1,4-dioxane were 1.0 g (2.3 mmol) of E6 and 0.68 g (2.7 mmol) of bis(pinacolato)diboron. Then, 92 mg (0.11 mmol) of PdCl$_2$(dppf) and 0.33 g (3.4 mmol) of potassium acetate were added, and the solution was stirred at 90 degrees Celsius for three hours. After cooling, toluene and water were added, the product was extracted with toluene, and the extract was dried with sodium sulfate. After the solvent was removed, the residue was purified by silica gel column chromatography (mobile phase: dichloromethane and heptane in a ratio of 1:2), thus yielding 0.80 g of E7 (yield: 72%).

[Chem. 18]

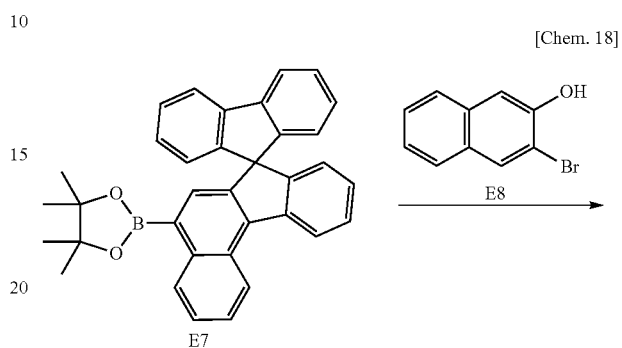

Put in 7 mL of toluene, 3 mL of ethanol, and 3 mL of 20% by weight aqueous sodium carbonate solution were 0.73 g (1.5 mmol) of E7 and 0.40 g (1.8 mmol) of E8. Then, 0.21 g (0.18 mmol) of tetrakis(triphenylphosphine)palladium(0) was added, and the solution was heated to 95 degrees Celsius and was stirred for two hours. After cooling, water and toluene were added, the product was extracted with toluene, and the extract was dried with sodium sulfate. After the solvent was removed, the residue was purified by silica gel column chromatography (mobile phase: chloroform and heptane in a ratio of 1:7), thus yielding 0.35 g of E9 (yield: 46%).

[Chem. 19]

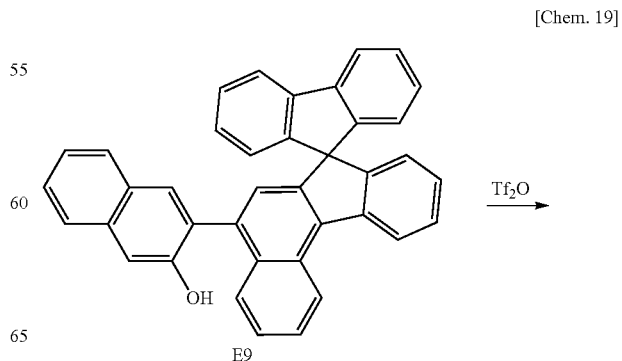

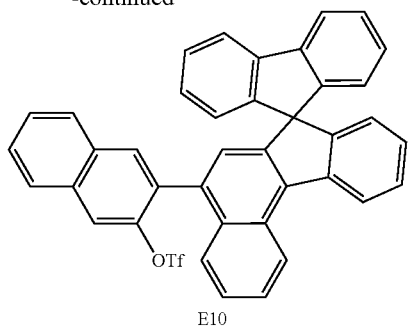

E10

After 0.35 g (0.69 mmol) of E9 was dissolved in 6 mL of pyridine and the solution temperature was set to 0 degree Celsius, 0.15 mL (0.89 mmol) of trifluoromethanesulfonic anhydride was gradually added dropwise. The reaction solution was stirred for two hours while gradually raising the solution temperature to room temperature. Water and toluene were added, the product was extracted with toluene, and the extract was dried with sodium sulfate. After the solvent was removed, the residue was purified by silica gel column chromatography (mobile phase: chloroform and heptane in a ratio of 1:3), thus yielding 0.25 g of E10 (yield: 56%).

[Chem. 20]

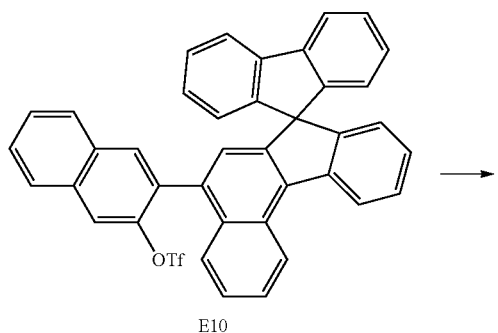

E10 → A1

Dissolved in 3 mL of N,N-dimethylformamide were 1.9 g (1.8 mmol) of sodium carbonate, 0.40 mL (3.7 mmol) of trimethyl orthoformate, and 0.11 mL (0.73 mmol) of DBU. The solution was stirred at 90 degrees Celsius for one hour. After cooling, 77 mg (0.11 mmol) of bis(triphenylphosphine)palladium(II) and 0.24 g (0.37 mmol) of E10 were added, and the solution was stirred at 140 degrees Celsius for three and a half hours. After cooling, water and toluene were added, the product was extracted with toluene, and the extract was dried with sodium sulfate. After the solvent was removed, the residue was purified by silica gel column chromatography (mobile phase: dichloromethane and heptane in a ratio of 1:4) and was recrystallized with toluene and methanol. The crystal was dried in a vacuum at 110 degrees Celsius and was purified by sublimation, thus yielding 66 mg of a pale yellow crystal of the exemplary compound A1 (yield: 37%).

The structure of the resultant compound was examined by nuclear magnetic resonance (NMR) spectroscopy: $^1$H NMR (CDCl$_3$, 500 MHz) σ (ppm): 8.67 (d, 1H, J=8.5 Hz), 8.41 (d, 1H, J=7.5 Hz), 8.26 (s, 1H), 8.07 (d, 1H, J=7.0 Hz), 8.01 (s, 1H), 7.95 (d, 2H, J=7.5 Hz), 7.84-7.89 (m, 2H), 7.75 (d, 1H, J=8.0 Hz), 7.48 (t, 1H, J=8.0, 7.5 Hz), 7.39-7.45 (m, 4H), 7.29 (s, 1H), 7.16 (t, 1H, J=7.5 Hz), 7.12 (t, 2H, J=7.5 Hz), 6.83 (d, 1H, J=8.5 Hz), 6.80 (d, 2H, J=7.5 Hz)

The emission spectrum of a toluene solution of the exemplary compound A1 in a concentration of $1\times10^{-5}$ mol/L was measured by photoluminescence spectroscopy at an excitation wavelength of 350 nm using F-4500 (manufactured by Hitachi, Ltd.). As a result, a blue emission spectrum having its peak intensity at 442 nm was obtained.

Example 2

Produced in this example was an organic light-emitting device including an anode, a hole injection layer, a hole transport layer, a light-emitting layer, a hole/exciton blocking layer, an electron transport layer, and a cathode in the above order. First, a pattern of ITO film having a thickness of 100 nm was formed on a glass substrate. The following organic layers and electrode layers were continuously formed on the substrate in a vacuum chamber at a pressure of $10^{-5}$ Pa by vacuum evaporation using resistance heating so that the electrodes faced each other over an area of 3 mm$^2$:

Hole transport layer (30 nm): G1
Light-emitting layer (30 nm): host: F11; guest: A1 (5% by weight)
Hole/exciton blocking layer (10 nm): G2
Electron transport layer (30 nm): G3
Metal electrode layer 1 (1 nm): LiF
Metal electrode layer 2 (100 nm): Al

[Chem. 21]

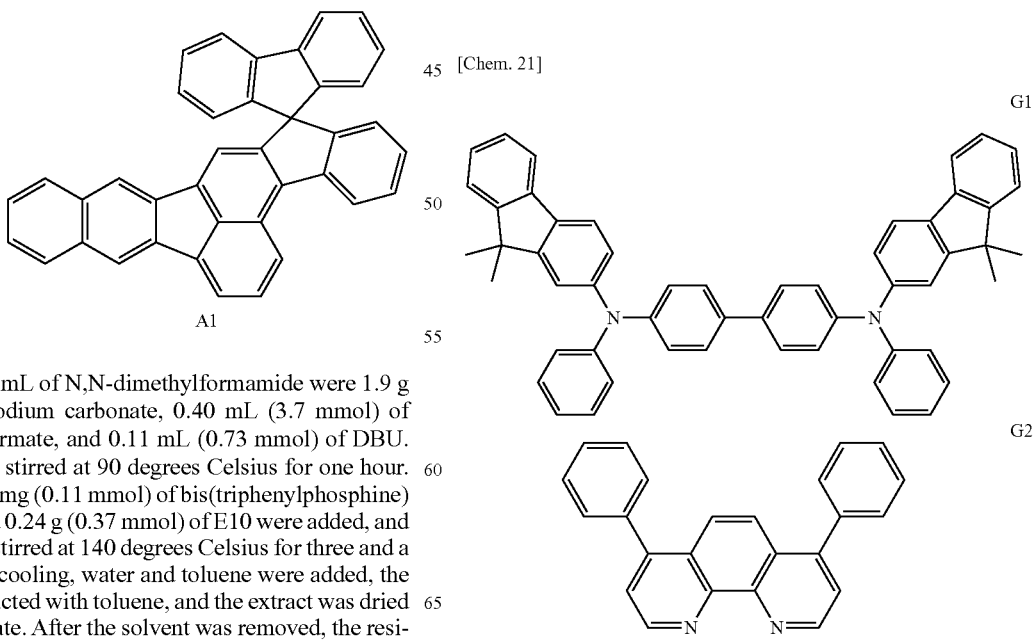

-continued

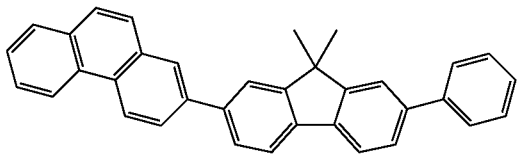

G3

The properties of the resultant organic light-emitting device were measured and evaluated. Specifically, the current-voltage characteristics of the device were measured using the microammeter 4140B (manufactured by Hewlett-Packard Company), and the luminous intensity of the device was measured using BM7 (manufactured by Topcon Corporation). As a result, excellent emission of blue light was observed with a luminous efficiency of 7.0 cd/A. In addition, the device was continuously driven at an initial luminance of 7,000 cd/m². As a result, the half-lifetime was 400 hours.

Example 3

Synthesis of Exemplary Compound A2

The exemplary compound A2 was synthesized and purified in the same manner as in Example 1 except that the organic compound E8 used in Example 1 was replaced with E11.

[Chem. 22]

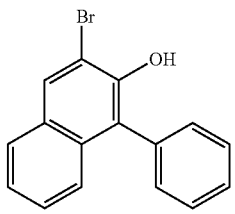

E11

The emission spectrum of a toluene solution of the exemplary compound A2 in a concentration of $1\times10^{-5}$ mol/L was measured by photoluminescence spectroscopy at an excitation wavelength of 350 nm using F-4500 (manufactured by Hitachi, Ltd.). As a result, a spectrum having its peak intensity at 444 nm was obtained.

Example 4

Produced in this example was an organic light-emitting device having the same structure as in Example 2 except that the organic compound A1 used in Example 2 was replaced with A2.

The properties of the resultant organic light-emitting device were measured and evaluated. The measurement methods were the same as those of Example 2. As a result, excellent emission of blue light was observed with a luminous efficiency of 7.4 cd/A. In addition, the device was continuously driven at an initial luminance of 7,000 cd/m². As a result, the half-lifetime was 430 hours.

RESULTS AND DISCUSSION

An organic compound according to the present invention is a novel compound having high quantum yield and emission properties appropriate for emission of blue light and can be used to produce an organic light-emitting device having excellent emission properties.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-021269, filed Feb. 2, 2010, which is hereby incorporated by reference herein in its entirety.

REFERENCE SIGNS LIST

8 TFT
11 Anode
12 Organic compound layer
13 Cathode

The invention claimed is:

1. An organic compound represented by general formula 1:

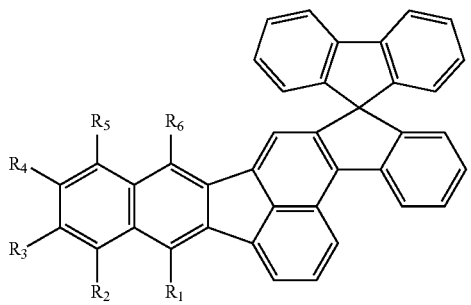

General formula 1 wherein $R_1$ to $R_6$ are each independently selected from a hydrogen atom, a substituted or unsubstituted alkyl group, and a substituted or unsubstituted aryl group.

2. An organic light-emitting device comprising a pair of electrodes and an organic compound layer disposed therebetween, the organic compound layer containing the organic compound according to claim 1.

3. The organic light-emitting device according to claim 2, wherein the organic compound layer is a light-emitting layer.

4. The organic light-emitting device according to claim 3, wherein the organic light-emitting device emits blue light.

5. A display apparatus comprising a plurality of pixels, each including the organic light-emitting device according to claim 2 and a switching device connected to the organic light-emitting device.

6. An image output apparatus comprising an image input unit configured to input an image and a display unit configured to output the image, the display unit having a plurality of pixels, each including the organic light-emitting device according to claim 2 and a switching device connected to the organic light-emitting device.

7. An illuminating device comprising the organic light-emitting device according to claim 2.

8. An exposure light source of an electrophotographic image-forming apparatus, wherein the exposure light source comprises the organic light-emitting device according to claim 2.

9. An electrophotographic image-forming apparatus comprising an exposure light source, wherein the exposure light source comprises the organic light-emitting device according to claim 2.

* * * * *